US008771658B2

(12) United States Patent
Humphreys et al.

(10) Patent No.: US 8,771,658 B2
(45) Date of Patent: Jul. 8, 2014

(54) COMPOSITIONS AND METHODS FOR TREATING KERATIN BASED FIBERS

(75) Inventors: James Humphreys, Victoria (CA); Jospeh Sherman, Tarzana (CA)

(73) Assignee: Coolway Inc., Tarzana, CA (US)

( * ) Notice: Subject to any disclaimer, the term of this patent is extended or adjusted under 35 U.S.C. 154(b) by 72 days.

(21) Appl. No.: 13/275,304

(22) Filed: Oct. 17, 2011

(65) Prior Publication Data
US 2012/0093755 A1 Apr. 19, 2012

Related U.S. Application Data

(60) Provisional application No. 61/393,809, filed on Oct. 15, 2010, provisional application No. 61/415,306, filed on Nov. 18, 2010, provisional application No. 61/496,424, filed on Jun. 13, 2011.

(51) Int. Cl.
*A61K 8/64* (2006.01)
*A61K 8/00* (2006.01)

(52) U.S. Cl.
USPC ............................ 424/70.14; 424/70.1

(58) Field of Classification Search
USPC .............................. 424/70.14, 70.1
See application file for complete search history.

(56) References Cited

U.S. PATENT DOCUMENTS

| | | | |
|---|---|---|---|
| 3,975,515 A | 8/1976 | Wajaroff et al. | |
| 4,077,441 A | 3/1978 | Rosen et al. | |
| 4,850,577 A | 7/1989 | Yamaoka | |
| 5,270,520 A | 12/1993 | Barzilai et al. | |
| 5,393,520 A | 2/1995 | Incando | |
| 5,554,838 A | 9/1996 | Berdich | |
| 5,587,155 A * | 12/1996 | Ochiai et al. ............... | 424/70.28 |
| 5,690,921 A * | 11/1997 | Lang et al. ................. | 424/70.13 |
| 5,972,356 A | 10/1999 | Peffly et al. | |
| 6,125,856 A * | 10/2000 | Yamashita ................... | 132/204 |
| 6,346,234 B1 | 2/2002 | Rollat et al. | |
| 7,431,947 B2 | 10/2008 | Gallmann | |
| 2005/0169862 A1 | 8/2005 | De La Mettrie | |
| 2005/0214239 A1* | 9/2005 | Nojiri et al. ................. | 424/70.12 |
| 2006/0008437 A1* | 1/2006 | Robinson et al. ............ | 424/70.1 |
| 2008/0279804 A1 | 11/2008 | Parker et al. | |
| 2009/0041868 A1* | 2/2009 | Brown et al. ................. | 424/725 |
| 2009/0110705 A1* | 4/2009 | Ho et al. ....................... | 424/401 |
| 2009/0126756 A1 | 5/2009 | Syed et al. | |
| 2009/0165812 A1 | 7/2009 | Resnick et al. | |
| 2010/0300472 A1 | 12/2010 | Malle et al. | |
| 2011/0011847 A1 | 1/2011 | Soerensen et al. | |
| 2012/0312320 A1 | 12/2012 | Humphreys et al. | |

FOREIGN PATENT DOCUMENTS

| | | |
|---|---|---|
| JP | 05-121152 | 5/1993 |
| KR | 2010-0084657 | 7/2010 |
| WO | 2012-051629 | 4/2012 |
| WO | 2012-174168 | 12/2012 |

OTHER PUBLICATIONS

Aarhus, How to Shampoo Your Hair, http://womenshair.about.com/od/shampoo/a/how2shampoo.htm, May 2008, retrieved online on Jul. 16, 2013.*
Dow Corning, Formulation Information: Conditioner, Dow Corning® 2-2078 Fluid, "Combing Cream for Kinky Hair: Combing Cream: Volume Control/Reduction, Formulation 01014", printed from the internet https://www.dowcorning.com/content/publishedlit/FORMUL_01014.pdf (copyright 2007).
Dow Corning, Formulation Information: Ethnic Hair Care, Dow Corning® 2-2078 Fluid, "Hair Treatment Cream for Curly Hair, Hair Treatment Cream: Strengthening, Volume, Control/Reduction, Formulation 01027", printed from the internet https://www.dowcorning.com/content/publishedlit/FORMUL_01027.pdf (Jun. 4, 2008).
Dow Corning, Formulation Information: Ethnic Hair Care, Dow Corning® 8500 Conditioning Agent, "Hair Treatment Cream for Curly Hair, Hair Treatment Cream: Color Protection, Heat Protection, Formulation 01028", printed from the internet https://www.dowcorning.com/content/publishedlit/FORMUL_01028.pdf (May 28, 2008).
Dow Corning, Formulation Information: Ethnic Hair Care, Dow Corning® 2-2078 Fluid, "Relaxer: Relaxing Effect, Formulation 00567", printed from the internet http://www.dowcorning.com/content/publishedlit/00567.pdf (Sep. 7, 2004).
Dow Corning, Formulation Information: Conditioner, Dow Corning® 8500 Conditioning Agent, "Rinse-Off Conditioner: Enhanced Wet Combing, Formulation 01395", printed from the internet http://www.dowcorning.com/content/publishedlit/FORMUL_01395.pdf (2007).
Dow Corning, Product Information: Personal Care, "Dow Corning® 2-8566: Amino Fluid", Ref. No. 22-1830E-01, printed from the internet http://www1.dowcorning.com/DataFiles/090007c8802c347a.pdf (Nov. 11, 2003).
Dow Corning, Product Information, "Dow Corning® 5-7113 Silicone Quat Microemulsion", Ref. No. 27-1104C-01, printed from the internet http://www2.dowcorning.com/DataFiles/090007c8800c8434.pdf (Nov. 13, 2006).
Dow Corning, "Make Your Hair Care Products Shine: Dow Corning® 2-2078 Fluid", Form No. 27-1159D-01, printed from the internet https://www.dowcorning.com/content/publishedlit/27-1159-01.pdf (2004, 2009, 2011, 2012).
Dow Corning, Formulation Information: Conditioner, Dow Corning® CE-7080 Smart Style, "Damage-Defying Hair Repair Cream: Ideal for Damaged and/or Curly Hair, Formulation 01534", printed from the internet http://www.dowcorning.com/content/publishedlit/FORMUL_01535.pdf (2010).

(Continued)

*Primary Examiner* — Blessing M Fubara
*Assistant Examiner* — Jennifer A Berrios
(74) *Attorney, Agent, or Firm* — Nixon & Vanderhye P.C.

(57) ABSTRACT

Compositions, formulations, kits and methods for temporarily or semi-permanently transforming the shape of individual hair filaments or keratinous fibers (curling, waving or straightening) by applying no heat or heat below about 300° F. to prevent damage to the keratinous fibers.

12 Claims, No Drawings

(56) References Cited

OTHER PUBLICATIONS

International Search Report issued in PCT/US2011/056602 dated May 31, 2012 (3 pages).
International Search Report issued in PCT/US2012/042324 dated Jan. 29, 2013 (3 pages).
Marchioretto et al., "Silicones are Versatile Solutions to Protect Hair", HAPPI.com, printed from the internet www.happi.com/articles/2009/02/silicones-are-versatile-solutions-to-protect-hair (printed Apr. 3, 2013).
R.A. Fischer Co., "Hair Conductivity Test", printed from the internet www.rafischer.com/hairtest.htm (1998).
Toyanik et al., "Molecular Mobility and Structure in Water-Acetone Mixtures", *Zhurnal Strukturnoi Khimii*, 28(5):94-100 (1987) English Translation.
Wortmann et al., "The Effect of Water on the Glass Transition of Human Hair", *Bioploymers*, 81:371-375 (2006).
Cao, Jinan, "Melting study of the $\alpha$-form crystallites in human hair keratin by DSC", *Thermochemica Acta*, 335:5-9 (1999).

* cited by examiner

COMPOSITIONS AND METHODS FOR TREATING KERATIN BASED FIBERS

CROSS REFERENCE TO RELATED PATENT APPLICATIONS

This application is related to, and claims the benefit of, U.S. Provisional Patent Application No. 61/393,809, filed Oct. 15, 2010, U.S. Provisional Application No. 61/415,306, filed Nov. 18, 2010, and U.S. Provisional Application No. 61/496,424, filed Jun. 13, 2011. Each of the above-identified priority patent applications is incorporated herein by reference in its entirety.

BACKGROUND

Heat-assisted styling of keratinous fibers (e.g., human hair), particularly using blow dryers, hair straighteners (flat irons), curling devices, heated comb, heated brush (with or without a rotating drum), or other heating means (each of which may be referred to herein as a "Hot Tool"), is prevalent amongst consumers. Unfortunately, heat-assisted styling can dry out and damage hair by subjecting the hair to too much heat. For example, hair can become over dried by holding a blow dryer too close to the hair, or by holding a Hot Tool too long at a particular spot of the hair. The overheating causes moisture to evaporate or be driven out of the hair so that the hair becomes brittle and more susceptible to cracking. In addition, overheating in heat styling can cause physical damage to the hair, particularly by raising the cuticles and/or creating blisters on individual hair fibers, thus causing increased friction between the hair fibers, making it more difficult to comb, requiring increased force to comb the hair, which in turn can wear the outer surface of the hair and cause cracks and breaks in the hair. For years, researchers assumed that human hair was similar in temperature based properties as wool as both are composed of the keratin protein. Recent research reveals that hair exhibits the following characteristics in response to heating:

Stage 1—at or below about 150° C. (302° F.), loosely bound water and tightly bound water is lost or evaporated from the hair.

Stage 2—at between about 160° C. and 175° C. (320° F.-347° F.), hair undergoes a glass transition phase—the hair begins to flow as hot glass would. At this glass transition temperature, plastic deformation of the hair is possible. In a 'normal' hydrated state, hair is elastic and can stretch and return back to its original length. Hair exhibits temporary plasticity which is why styles like curls, and twist outs/knot outs can occur. However, at this glass transition temperature, the plasticity of hair is not temporary. Upon cooling, the hair may return to a "normal looking" state, but the hair shaft has been damaged.

Stage 3—at between about 215° C. and 235° C. (419° F.-455° F.), the keratin, which is present in all hair as a natural alpha helix (α-helix), melts, thereby leaving the hair in a permanently damaged state.

Currently, styling of hair is done using tools emitting relatively high heat operating at temperatures over 300° F. to achieve said glass transition/transformation temperature, causing heat damage to hair in the process of styling. When using heat to style hair (or other keratinous fibers), the required temperature to reach a glass transition temperature is proportional to the water saturation or moisture content (i.e., water content) of the keratin fibers. As the water saturation or moisture content increases, the temperature that is required to reach a glass transition temperature decreases. As such, it would be advantageous to use the lowest possible temperature at which styling of the keratinous fibers can be achieved in order to prevent undesirable heat damage, which occurs at temperatures above 300° F., by temporarily increasing the humidity or moisture level in hair.

Persons having naturally curly or wavy hair often desire to alternate, at will, between having a curly or straight (i.e., non-curly) hair style configuration. There is a growing demand for products that can safely and temporarily remove some or all of the natural curl from the hair while at the same time provide the consumer with versatility in styling the hair.

Hair styling or hair setting compositions are widely used by consumers in the cosmetic industry to retain a particular shape or style of the hair. Hair styling compositions can assist in manipulating or styling the hair, providing temporary benefits in holding the shape of the hairstyle (fixing) and/or maintaining the shine or appearance (grooming, restyling) of the hair, e.g., in the evening, during the day, between hair washing periods, or between subsequent hair setting procedures. The inherent problem encountered in hair setting is the natural tendency of the hair to return to its natural shape. For example, the styled or set hair returns to its natural shape almost immediately if moistened. Likewise, high humidity conditions accelerate the tendency of the hair to return to its natural shape. When the hair returns to its natural shape, getting it back to its setting requires repeating the process of styling the hair or a part of, also known as "touching up the hair". Intensive efforts have been directed toward providing a hair set with sufficient holding power to maintain the designed hair style until at least the next shampoo, and, therefore, giving the styled hair set a degree of permanency. Therefore, investigators have sought to delay the combined action of natural forces and moisture that causes the hair to return to its original state by applying solutions containing naturally-occurring or synthetic polymers after the hair is shaped into a desired configuration. When applied to the shaped hair from aqueous or aqueous/alcoholic solutions (setting lotions), the polymers leave a film on the hair, after drying, to help maintain the hair in the previously shaped configuration. The polymeric film promotes cohesion and gives stability to the hair set to maintain the hold of the hair set. The principal objective of a setting lotion is to cover the previously styled hair with an invisible polymeric film that will give the styled hair a degree of rigidity and protect the hair style against wind and humidity. A problem created by the methods described is the weighing down of hair by the film covering the hair, creating less movement of hair and/or rigidity which are not desired by consumers.

The art of temporarily removing the natural curl from naturally curly hair was practiced, in the early days, by applying a pomade to the hair and then straightening the curl by combing the pomade coated hair, under tension, using a heated metal comb, a process commonly referred to as "pressing." Although pressing left the hair shiny, silky and temporarily straightened, the process was cumbersome and caused hair damage from excessive heating. The pomades were cosmetically unaesthetic greases and difficult to remove from the hair. Additionally, the metal combs were heated, either electrically or on a stove, to relatively high temperatures, which posed the risk of burning the unprotected skin and scalp or of singeing the hair. More recently, some progress was made using a hair ironing process employing oily lotions and electrical variable heating devices, known as flat hair irons, and hair irons, some of which are combination hair straightener and curling irons, that can be controllably heated. However, the configuration of hair that has been temporarily straightened by these procedures reverts to its natural curly or wavy configuration readily on exposure to humidity, or perspiration, and especially upon washing the hair, as well as the damage caused by the use of these tools at temperatures over about 300° F. still renders the process as not completely satisfactory.

Permanent waving and straightening of hair are common techniques for beautifying hair or fur by permanently forming or setting the hair or fur into a desired configuration. Various techniques have been practiced for many years in the hair and fur industries, such as in hair salons, and in the home practiced by an individual. Hair and fur is comprised of keratin, which is a polyamide cross-linked by disulfide bonds. The disulfide bonds are responsible for the hair or fur being maintained in a particular configuration. In a conventional hair waving or straightening process, the hair is first softened or relaxed by breaking the disulfide bonds in the keratin with a reducing agent and then hardening the hair or fur in the desired configuration by stopping the reduction reaction and restoring or reforming disulfide bonds by applying an oxidizing agent, generally referred to in the art as a neutralizer.

A "Brazilian" hair straightening treatment has been described that requires the use of a formaldehyde solution in conjunction with a heated flat iron set at a temperature of about 232° C. (449.6° F.), to achieve temporary hair straightening with some resistance to reversion. In this process, solutions of formaldehyde (1.5% to 5%) are used which straighten the hair, which lasts through about two to about three shampoo sessions, or about four weeks, before having to repeat the straightening process. Formaldehyde is known to form cross-links among protein end groups to create a stable, complex matrix. For example, formaldehyde can form cross-links between amide, amino, and tyrosine groups, S—CH2-NH cross-links between N-terminal cysteine and amine groups, NH—CH2-NH cross-links between amine groups, and S—CH2-S cross-links. A variation of this procedure has been used in which the hair is first swollen with a composition, referred to in the trade as a dilator, having a pH of about 8.5, rinsed, then treated with a "no-frizz" lotion containing 0.2% formaldehyde, along with a thermal protector lotion containing silicones, and the hair is then blow dried and flat ironed. The hair treated in this manner required repeating the treatment process weekly to progressively attain some level of discernible straightening over a period of four consecutive weeks. Upon stopping usage of the procedure, however, the configuration of the hair reverts to its original wavy or curly pattern after two to three shampooings.

Cross-links produced by formaldehyde are not stable to acid or alkaline hydrolysis, and in aqueous solution, formaldehyde undesirably forms methylene glycol and can react with oxygen to produce formic acid. Additionally, exposure to formaldehyde solutions raises health concerns to the users and practitioners, because formaldehyde generally is presumed to be a carcinogen (i.e., causes cancer), and can cause contact dermatitis. Thus, a formaldehyde-containing solution is toxicologically unacceptable and, in many countries, including Brazil, the amount permitted to be present in hair and skin care products topically applied to humans is controlled and amounts exceeding the allowable level are prohibited. While hair straightened by the foregoing Brazilian processes was silky, straight and shiny, the amount of formaldehyde used exceeds the permissible amount of 0.1% free formaldehyde in cosmetics in Brazil, making it cosmetically undesirable. In Canada the Brazilian treatment was banned by Canadian health authorities in October, 2010. Another concern for users is that the extremely high heat used in the process as well as the chemicals used causes damage to hair, and many users are unhappy with their long term results using this process. The commercial success of the Brazilian treatment has created a great demand for flat irons working at higher temperatures of up to 232° C. (449° F.), shifting the market and getting most of the flat irons made to reach this high heat, keratin melting, and hair damaging temperatures.

Conventional chemical relaxers (hair straighteners) that are formulated to remove substantially all natural curl from the hair are well known in the art and typically contain inorganic or organic bases that convert the disulfide bonds of cystine in hair to stable, irreversible crosslinks of primarily lanthionine by the action of hydroxide ion. These lanthionizing chemical relaxers generally are highly alkaline, typically in the range of about pH 12 to about pH 14 and, and typically produce a straight textural configuration that is substantially permanent (i.e., irreversible). Some consumers, however, do not wish to be committed to just one texture and some are increasingly hesitant to risk exposing their hair and scalp to possible damage from such high alkalinity. As such, an alternative to lanthionization relaxers is a chemical keratin reduction-oxidation relaxer process. Conventional commercial reduction-oxidation processes typically reduce the disulfide bonds in the hair with thiol salts, usually ammonium thioglycolate in a viscous medium at an alkalinity typically in the range of about 9 to about 9.5. The reduced hair is mechanically straightened with combing, and then oxidized with hydrogen peroxide or sodium bromate to restore the disulfide bonds in the new straightened configuration. The straightening effect lasts through about three to four shampooings, but generally provides a less permanent straightening effect than that achieved by lanthionization, which damages hair by destroying the natural cysteine groups or disulfide bonds that account for hair's strength, and most of its toughness and abrasion resistance. One attempt to avoid conventional lanthionizing chemical relaxer was a multiple-step, heat-assisted, reduction-oxidation process. The hair was chemically reduced with an ammonium thioglycolate cream composition, shampooed, dried with a hair dryer, mechanically straightened with a heated flat iron set at a temperature of about 200° C., then chemically oxidized with a sodium bromate or hydrogen peroxide lotion, dried with a hair drier, and again mechanically straightened with the heated flat iron. This process, however, was tediously long, taking between four and six hours to complete, and chemical damage as well as high heat damage was not avoided.

Various methods are used to measure the efficacy of a hair-styling composition. One method commonly employed to objectively test the efficacy of hair styling compositions involves measuring curl retention under humid conditions. Another method involves semi-permanent hair straightening using a flat iron followed by several wash-out steps. Additional methods of subjective evaluation may be employed that include, for examples: visual and tactile sensory methods (e.g., by visual examination and touching) for characteristics such as appearance (shine, cleanliness, naturalness of appearance and texture), feel (stiffness, tackiness, softness), curl memory (bounce, and restylability), straightness memory (flatness), ease of combing and brushing the hair, residue (flaking), static, smoothness, and the like. Also of importance are the aesthetic characteristics and appearance provided by hair styling compositions before, during, and after application to hair. The product viscosity should be non-runny to avoid dripping during application. The product should be easy to spread, have a smooth texture, a non-tacky feel, and be able to dry relatively quickly on the hair.

Providing hair styling compositions that exhibit good high humidity curl and/or straightness retention while maintaining desirable subjective properties, e.g., smooth texture, curl memory, bounce, naturalness of appearance, etc., has been difficult to achieve with conventional hair-setting compositions. If left untreated, hair often becomes tangled when wet and/or dry such that combing and brushing of the hair is difficult. Furthermore, hair frequently exhibits poor electrostatic properties such that it is susceptible to "scattering", especially in low humidity environments. In addition, conventional hair straightening and conditioning compositions generally contain man-made chemicals that often leave the hair undesirably harsh, dull, and dry. In addition, conventional hair straightening involves high heat temperatures over 300° F., which undesirably damages hair and other keratinous fibers.

There is an ongoing need and desire, therefore, for cosmetically acceptable compositions and convenient practical processes that temporarily remove some or all of the natural curl from naturally curly hair, and provide some resistance to curl reversion on exposure to humidity, perspiration, or washing, and yet provide the user with versatility in alternating between a straight or curly hairstyle.

To address the above and other shortcomings, below are provided compositions, kits, tools and/or methods for styling hair and other keratin-based fibers without the use of temperatures above about 300° F., or with no heat at all, which are capable of providing, among other things, high humidity curl and/or straightness retention, versatility in alternating between straight or curly hairstyles from wash to wash so the end user would not need to touch up the hair between washes, but have the ability to change hair style from curly to straight and vice versa at will with hair washing/shampooing as the reset event. The example embodiments below include compositions and methods for achieving high humidity curl and/or straightness retention without coating the hair with film, thereby achieving a benefit of hair feeling weightless. The example embodiments may overcome one or more of the limitations and disadvantages in the art of hair care by providing thermal hair straightening and conditioning compositions that can be applied before, and during thermal straightening to render the hair smoother, shinier, softer, and more manageable, to minimize static charge, tangling, and scattering of the hair, such that the hair becomes smooth and straight after application. Further, the styling compositions and processes disclosed herein avoid the deleterious action that can be caused by conventional high heat treatments or highly alkaline lanthionization chemical hair relaxer processes, as readily determined by measured changes in the physical, mechanical integrity of the keratin fibers. Measurable changes in the integrity of the hair include desirable changes in tensile strength properties (increased about 5% to 20%), elasticity, porosity, cuticle erosion, fiber breakage, wet and dry combing force and the like, as well as changes in discernible subjective properties, i.e., tactile feel, and visible sheen or appearance.

As a result, the styling compositions and methods may provide substantially increased body to keratinous fibers, especially human hair; provide better uptake of protein monomers or polymers onto the hair; provide a polymer coating with less flaking; provide a more complete attachment of the resulting polymer to the hair, better protect the hair against uptake of humidity; strengthen damaged hair; resist removal through at least several shampooings; prevent leach out of hair colors; provide for higher loading of polymer into and onto the hair and, therefore, better set retention; protect the hair against thermal damage by completely avoiding high heat damaging temperatures typically used for styling hair (i.e., above about 300° F.) and better resist hair uptake of atmospheric contaminants.

DESCRIPTION OF EXEMPLARY EMBODIMENTS

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

In a general sense, described herein are aqueous or non-aqueous based, keratin-protecting, styling compositions and methods that minimize or eliminate the curl configuration in naturally curly hair (including non-hair keratin-based fibers) by loosening or removing some or all of the natural wave or curl pattern, while substantially retaining desirable properties, e.g., strength and sheen. The styling composition could also assist in imparting a wave or curl pattern to straight hair. The styling composition may also contain a fixing agent, as described below, and other cosmetically acceptable solvents, containing a suitable polymerizable protein, oligomer, peptide, or monomer (e.g., silk peptide or hydrolyzed silk) that is applied onto keratin fibers to modify one or more cosmetic properties of the keratinous fibers. The protein or peptide is polymerized, in-situ, while in contact with the hair to modify at least one hair property, such as body, conditioning, shine, set retention, comb-ability, or the like. The protein, oligomer, peptide or monomer can be polymerized, in-situ, while in contact with hair in any known manner, such as by including an initiator, e.g., a heat-activated initiator, or a polymerization catalyst or fixing agent in the styling composition and processing the composition, such as by heating the composition or keratinous fiber with warm water, blow dryer, heated comb, heated brush (with or without a rotating drum), flat iron, curling iron or other heating means or by use of an accelerator or catalyst, or the like, e.g. mechanical force, ultrasound and other energy imparting tools and means.

In an example embodiment, there is provided hair styling composition capable of imparting a firm and silky look and feel to hair and inhibits frizz. The hair styling composition may be used during hot iron and after hot iron straightening of curly hair to impart a smooth and silky feel to hair. In some embodiments, the hair-styling method exhibits at least semi-permanent hair straightening (or curling) after at least about three wash cycles comprising shampoo and conditioner treatments and after exposure for over about 12 hours to a high humidity environment, conditions including 90% Relative Humidity and a temperature of about 75° F., [24° C.].

The styling process optionally is heat-assisted using relatively low heat (e.g., below about 300° F.) to provide a substantially straightened or curled fiber that lasts until the next washing. Thus, the styling compositions temporarily remove the natural curl but permit the straightened hair to revert to its original natural curl configuration upon discontinuing use of the styling composition and process.

The keratin-protective, styling compositions contain an effective styling (straightening, curling or waving) amount of a physiologically tolerable, fixing agent capable of forming or causing cross-links with proteinaceous hair keratin. The effective amount used includes an amount that is effective to retain hair-styling, such as e.g., straightness retention or curl retention, through at least one or more washing cycles. The fixing agent is selected from the group consisting of $(CH_3)_2CO$ (a.k.a., $(CH_3)_2CO$, dimethyl ketone, β-Ketopropane, Propanone, 2-Propanone and acetone, etc.), ethyl lactate, butyl lactate, butanone, ethanol, t-butanol, and n-butanol. Without wishing to be bound by any theory, it is believed that the fixing agent is, in one aspect, a keratin cross-linking agent of low molecular weight capable of causing relatively fast crosslinking of keratin at a given temperature and pressure to form cross-linkages. The fixing agent is believed to be capable of initiating an in-situ polymerization of endogenous and exogenous proteins or peptides that are present on the hair shaft or added to the styling composition. Additionally, the crosslink density or number of cross linkages formed in the keratin network may be affected by other factors including a) the concentration of the cross-linking agent in the fixative solution, b) the pH of the fixative solution, and c) any alteration or change in the physical conditions such as temperature and pressure. In any event, the fixing agent must be present in the styling composition in amount of about 10% to about 45% by weight, including all sub ranges therebetween.

The term "peptide" refers to two or more amino acids joined to each other by peptide bonds or modified peptide bonds. The term "hair-binding peptide" refers to peptide sequences that bind with high affinity to hair. The hair-binding peptides of the invention are from about 7 amino acids to about 50 amino acids, optionally from about 7 amino acids to about 25 amino acids, optionally from about 7 to about 20 amino acids in length. The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

It is believed that peptides having high concentrations of glutamic acid and aspartic acid will allow more fixing of exogenous protein and provide for hair repair properties due to a condensation reaction that is believed to take place between the carboxylic acid group of the amino acids compounds and an available amine group found in keratin fibers. Examples of peptides that would have high concentrations of glutamic acid and aspartic acid would be corn, soy, nut and seaweed proteins, as well as Porphyra (sea weed).

Other suitable monomers include acrylic or methacrylic acid esters of Cx-C18 alcohols, such as methanol, ethanol, 1-pro-panol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri-methyl-1-hexanol, 1-decanol, and the like, the alcohols having from about 1-18 carbon atoms with the average number of carbon atoms being from about 4-12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and methoxy ethyl meth¬ acrylate. The polymers hereof can be homopolymers of such hydro-phobic monomers or can be co-, ter-, etc. polymers of hydrophobic monomers. Preferred monomers include n-butyl methacrylate, isobutyl methacrylate, 2-ethylhexyl methacrylate, methyl methacrylate, t-butylacrylate, t-butyl ethyacrylate, and mixtures thereof. Especially preferred are homopolymers of t-butylacrylate.

In particular, styling can be achieved within a practical time period. For instances, the hair can be contacted with the exemplary keratin-protective styling compositions for any effective amount of time, e.g. from about 1 minute to about 120 minutes, from about 1 minutes to about 20 minutes, or from about 5 minutes to about 10 minutes, and all subranges therebetween. The styling compositions retain the desirable properties of the natural intact hair, such as tensile strength, shine, and softness, and substantially maintain the original, natural color or tone of the hair. The styling compositions can be used in heat-assisted procedures either as the primary or sole style-imparting agent or in conjunction with reduction-oxidation processes. The keratin-protectant styling compositions can beneficially provide the user with the ability to alternate between having a substantially straight hair style and a curly or wavy hair style or vice-versa, as desired, over selected periods of time. The keratin-protectant styling compositions can provide temporary or semi-permanent straightening, curling or waving sufficient to withstand one or more exposures to humidity and perspiration. In one useful aspect, washing treated hair will revert the styled hair to its original natural curl or wave pattern. The heat-assisted styling procedure using the exemplary keratin-protective, styling compositions provides a convenient and easy-to-use system for versatility in styling keratinous fibers, such as human hair. The composition may also contain, but is not limited to, as further exemplified herein, amino acids of human hair keratin, bio-extenders, oligomer elements of marine algae, vitamin-E, silicones, water, fragrance, etc. They may also comprise one or more surfactants, one or more emollients, one or more emulsifiers, one or more skin cleansing agents, one or more preservatives, and/or one or more aqueous based diluents. They may also contain one or more thickeners.

In accordance with one example embodiment, heat is applied to hair treated with the styling composition with or without an additional conditioning agent. The heat is applied in amount effective to at least semi-permanently style the hair, and the hair is accordingly styled. An effective amount of heat may be applied by contacting the hair with a Hot Tool at a temperature (e.g., the surface temperature of the portion of the device that contacts the hair) of at least about 212° F. to about 300° F. (100° C. to about 150° C.) and all subranges therebetween, for an effective time period (e.g., for at least about 1 second). To prevent undesirable damage to hair, temperatures above about 300° F. (about 150° C.) and time periods above about five (5) minutes should be avoided. The heat also can be applied for an effective time period, for example, by passing or drawing a device (e.g., a flat iron) through a section of hair (e.g., lengthwise and with a combing motion through the hair while the styling surface of the device remains in contact with at least a portion of the hair during each pass) at an appropriate rate, e.g., for from about 2 seconds to about 10 seconds or more. It will be appreciated that the time period required for contacting the hair with a heat-styling device, to semi-permanently style hair or other keratinous fiber, can depend on a number of factors. Such factors can include, e.g., the nature and extent of chemical treatment on the hair, the type and condition of hair involved, the length of the hair (which, of course, may impact the rate and length of time required for each pass for certain styling devices), the temperature of the device, the nature of the device, and other factors. For example, a suitable heat-styling method for straightening hair includes passing the hair through a flat iron at less than about 150° C. over the hair at least one time for 1-10 seconds per pass.

The styling can include contacting the hair with a shaped surface so as to manipulate the hair to conform to the shape of the surface. If desired, heat can be applied directly to the hair by contacting the hair with a heated shaped surface, which can also be used to style and manipulate the hair to conform to the shape of the surface. Thus, in some embodiments, the shaped surface is heated and the heat is applied to the hair with the shaped surface. If desired, the heat application and styling can be performed simultaneously. Heat can also be applied via an indirect heat source such as, for example, blow dryers, hood dryers, heating caps, steamers, and combinations thereof. In some embodiments, it can be desirable to use a combination of direct and indirect heat sources. When using a shaped surface, a straight surface may be used for straightening hair and a curved surface may be used for curling hair, or a combination of such surfaces may be used, if desired. Optionally, the heat can be applied in multiple stages or passes. Such stages or passes can include applying heat to the hair and styling as described herein at least two times, e.g., so as to apply heat and to manipulate the hair to conform to the shape of a surface with intermediate removal of the heat source between stages or passes. Accordingly, in some embodiments, the heat application and styling are performed two or more times. In other embodiments, the heat application and styling are performed three or more times. For example, when using a flat iron to straightening the hair, two passes of the iron over or against the hair can be performed, and in some instances three passes of the iron over or against the hair can be performed.

Carriers. In example embodiments, the styling composition may comprise a carrier component taken alone or in any suitable combination. Suitable carriers can include, for example, aqueous carriers that can include any suitable quantity of water, e.g., from about 25 wt % to about 95 wt % water, from about 30 wt % to about 95 wt % water, or from about 40 wt % to about 60 wt %, and all subranges therebetween. Suitable carriers can include solvents such as alcohols, polyols, or mixtures thereof. Exemplary alcohols include methanol, ethanol, propanol, and butanol. Exemplary polyols include polyalkyl glycols such as ethylene glycol, propylene glycol, butylene glycol, and glycerine. In some embodiments, the carrier is water alone. In some embodiments, the carriers include aqueous solutions of solvents that can be present in either composition used in accordance with the example methods, e.g. in an amount of from about 25 wt % to about 97 wt % solvent, from about 30 wt % to about 95 wt % solvent, or from about 40 wt % to about 60 wt % solvent and all subranges therebetween.

Conditioning Agents. Suitable conditioning agents may be added, and may include, for example, one or more amphoteric copolymers, one or more amphoteric terpolymers, one or more cationic conditioners and the like, and combinations thereof. Suitable conditioning agents can include amphoteric terpolymers of acrylic acid, diallyl dimethyl ammonium chloride, and acrylamide. The styling composition can include one or more additional conditioning agents in an amount, e.g., from about 0.01 wt % to about 20 wt %, e.g., from about 0.01 wt % to about 15 wt %, or, e.g., from about 0.05 wt % to about 10 wt %. An exemplary conditioning agent is polyquaternium-39. Other exemplary products that may serve as conditioning agents include polyquaternium-4 and/or VP/dimethylaminoethyl methacrylate copolymer 845-G, and the like. Hair conditioners as herein defined are agents which improve the appearance, texture, and sheen of hair as well as increasing hair body or suppleness. Other suitable hair conditioners, include, but are not limited to, styling aids, hair straightening aids, hair strengthening aids, and volumizing agents, such as nanoparticles. Hair conditioners are well known in the art, see for example Green et al., supra, and are available commercially from various sources. More suitable examples of hair conditioners include, but are not limited to, cationic polymers, such as cationized guar gum, diallyl quaternary ammonium salt/acrylamide copolymers, quaternized polyvinylpyrrolidone and derivatives thereof, and various polyquaternium-compounds; long chain alkyl groups; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and nanoparticles, such as silica-nanoparticles and polymer nanoparticles. The suitable hair conditioners of the present invention contain amine or hydroxyl functional groups to facilitate coupling to the hair-binding peptides, as described below. Examples of suitable conditioners are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

Examples of other suitable conditioning agents that can be incorporated into the exemplary styling composition include, without limitation: a quaternary ammonium salt (e.g., quaternium-80 (i.e, Siloxanes and Silicones, dimethyl, 3-[3-[(3-coco amidopropyl)dimethylammonio]-2-hydroxypropoxy] propyl group-terminated, acetates (salts)) and the like); polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; cetyl trimethyl ammonium chloride; oleyl dimethyl benzyl ammonium chloride; oleyl alcohol; stearyl alcohol; stearamidopropyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris(oligoxyethyl)alkyl ammonium phosphate; an amino-functional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quaternium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl dimonium chloride; hydroxypropyl biscetyl dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1-20 moles) lanolin alcohols; isostearamide DEA; and hydrolyzed collagen protein. The presence of oligomer-reactive group(s) on any of these conditioning agents allows the conditioning agent to react with the oligomer during in-situ polymerization for incorporation into the polymer.

When one or more of these water-insoluble conditioning agents is included in the styling composition, optionally in an amount of about 0.5% to about 3% by total weight of the composition, the composition also can include a suspending agent for the conditioning agent, in an amount of about 0.5% to about 5%, by total weight of the composition. Such suspending agents also may be useful for suspending solvent-insoluble oligomers. The particular suspending agent is not critical and can be selected from any materials known to suspend water or solvent-insoluble liquids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

Surfactants. Another ingredient which may be included in these hair styling compositions is one or more surfactants in an amount of from about 0.01 wt % to about 20 wt %, from about 0.01 wt % to about 15 wt %, or, from about 0.05 wt % to about 10 wt % of one or more surfactants. Surfactants are surface-active agents that are able to reduce the surface tension of water and cause the product to slip across or onto the skin. Surfactants also include detergents and soap. In one embodiment, the surfactants are amphoteric. Anionic or cationic surfactants may be used as well. Suitable surfactants can include one or more anionic, nonionic, cationic, and amphoteric surfactants, with nonionic, cationic, and amphoteric surfactants being suitable. Exemplary surfactants include PPG- 5/Ceteth 20, Oleth-20, polysorbate-20, and cocamidopropyl betaine. Other surfactants that may be used comprise, or alternatively include but are not limited to, 3-aminopropane sulfonic acid, almond amide DEA, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium cocomonoglyceride sulfate, ammonium coco sulfate, ammonium cocoyl isethionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide DEA, apricot amidopropyl betaine, arachideth-20, avocadamide DEA, avocadamidopropyl betaine, babassuamide DEA, babassuamidopropyl betaine, babassuamidopropylamine oxide, behenalkonium chloride, behenamide DEA, behenamide MEA, behenamidopropyl betaine, behenamine oxide, behentrimonium methosulfate, behenyl betaine, buteth-3 carboxylic acid, butyl polyglucose, C10-14 alkyl benzenesulfonic acid, CI 1-15 pareth-12, CI 1-15 pareth-20, CI 1-15 pareth-30, CI 1-15 pareth-40, CI 1-15 pareth-7 carboxylic acid, CI 1-15 pareth-9, CI 1-21-pareth-10, C12-13 pareth-10 phosphate, C12-13 pareth-5 carboxylic acid, C12-13 pareth-7, C12-15 pareth-11, C12-15 pareth-12, C12-15 pareth-2 phosphate, C12-15 pareth-7 carboxylic acid, C12-15 pareth-9, C12-15 pareth-9 hydrogenated tallowate, C14-15 pareth-13, C14-15 pareth-8 carboxylic acid, C22-24 pareth-33, calcium laurate, calcium myristate, canolamidopropyl betaine, caprylyl/capryl glucoside, caprylyl pyrrolidone, carboxymethyl isostearamidopropyl morpholine, cellulose acetate propionate carboxylate, ceteareth-100, ceteareth-15, ceteareth-17, ceteareth-2 phosphate, ceteareth-20, ceteareth-25, ceteareth-25 carboxylic acid, ceteareth-27, ceteareth-30, ceteareth-4 phosphate, ceteareth-40, ceteareth-5 phosphate, ceteareth-50, ceteareth-55, ceteareth-80, cetearyl polyglucose, ceteth-12, ceteth-14, ceteth-15, ceteth-16, ceteth-20, ceteth-24, ceteth-25, ceteth-45, cetethyl morpholinium ethosulfate, cetethyldimonium bromide, cetoleth-15, cetoleth-24, cetoleth-25, cetoleth-6, cetrimonium tosylate, cetyl betaine, cetyl PPG-2 isodeceth-7 carboxylate, cetylpyridinium chloride, cholesteryl/behenyl/octyldodecyl lauroyl glutamate, cocamide, cocamide DEA, cocamide MEA, cocamide MIPA, cocamidoethyl betaine, cocamidopropyl betaine, cocamidopropyl dimethylamine, cocamidopropyl dimethylamine dihydroxymethylpropionate, cocamidopropyl dimethylamine hydrolyzed collagen, cocamidopropyl dimethylamine lactate, cocamidopropyl dimethylamine propionate, cocamidopropyl dimethylaminohydroxypropyl hydrolyzed collagen, cocamidopropyl dimethylammonium C8-16 isoalkylsuccinyl lactoglobulin sulfonate, cocamidopropyl hydroxysultaine, cocamidopropyl lauryl ether, cocamidopropylamine oxide, cocamidopropyldimonium hydroxypropyl hydrolyzed collagen, cocamine oxide, cocaminobutyric acid, cocaminopropionic acid, coceth-4 polyglucose, coceth-7 carboxylic acid, coco/oleamidopropyl betaine, cocoamphodipropionic acid, cocobetainamido amphopropionate, cocobetaine, cocodimonium hydroxypropyl silk amino acids, cocoethyldimonium ethosulfate, coco-glucoside, cocohydroxysultaine, coco-morpholine oxide, coconut acid, coco polyglucose, coco-sultaine, cocotrimonium chloride, cocoyl benzyl hydroxyethyl imidazolinium chloride, cocoyl hydrolyzed collagen, cocoyl hydroxyethyl imidazoline, cocoyl sarcosinamide DEA, cocoyl sarcosine, corn acid, cyclopentane carboxylic acid, DEA-C12-15 alkyl sulfate, DEA-cetyl phosphate, DEA-cetyl sulfate, DEA-cocoamphodipropionate, DEA-cyclocarboxypropyloleate, DEA-dodecylbenzenesulfonate, DEA-isostearate, DEA-laureth sulfate, DEA-lauryl sulfate, DEA-methyl myristate sulfonate, DEA-myreth sulfate, DEA-myristate, DEA-myristyl sulfate, DEA-oleth10 phosphate, DEA-oleth-20 phosphate, DEA-oleth-3 phosphate, DEA-oleth-5 phosphate, deceth-4 phosphate, deceth-7 carboxylic acid, decyl betaine, decyl glucoside, decyl polyglucose, decylamine oxide, diammonium dimethicone copolyol sulfosuccinate, diammonium lauramido-MEA sulfosuccinate, diammonium lauryl sulfosuccinate, diammonium oleamido PEG-2 sulfosuccinate, diamyl sodium sulfosuccinate, dicapryl sodium sulfosuccinate, dicetyldimonium chloride, dicocodimonium chloride, dicyclohexyl sodium sulfosuccinate, didecyldimonium chloride, diethanolaminooleamide DEA, diethylamine laureth sulfate, diethylaminoethyl cocoate, diethylaminoethyl PEG-5 cocoate, diethylaminoethyl stearate, diheptyl sodium sulfosuccinate, dihexyl sodium sulfosuccinate, dihydrogenated CI6-18 amido benzoic acid, dihydrogenated tallow benzylmonium chloride, dihydrogenated tallow methylamine, dihydrogenated tallow phthalate, dihydroxyethyl CI2-15 alkoxypropylamine oxide, dihydroxyethyl C8-10 alkoxypropylamine oxide, dihydroxyethyl C9-11 alkoxypropylamine oxide, dihydroxyethyl cocamine oxide, dihydroxyethyl lauramine oxide, dihydroxyethyl soya glycinate, dihydroxyethyl stearamine oxide, dihydroxyethyl tallow glycinate, dihydroxyethyl tallowamine HC1, dihydroxyethyl tallowamine oleate, dihydroxyethyl tallowamine oxide, diisobutyl sodium sulfosuccinate, dilaureth-10 phosphate, dilaureth-4 dimonium chloride, dilauryldimonium chloride, dilinoleamidopropyl dimethylamine dimethicone copolyol phosphate, dimethicone propyl PG-betaine, dimethyl cocamine, dinonoxynol-9 citrate, dioctyl sodium sulfosuccinate, dioctyldodeceth-2 lauroyl glutamate, dioctyldodecyl lauroyl glutamate, dioleth-8 phosphate, dipropylene glycol salicylate, disodium bisethylphenyl triaminotriazine stilbenedisulfonate, disodium C12-15 pareth sulfosuccinate, disodium caproamphodiacetate, disodium caproamphodipropionate, disodium capryloamphodiacetate, disodium capryloamphodipropionate, disodium cetearyl sulfosuccinate, disodium cocamido MEAsulfosuccinate, disodium cocamido MIPA-sulfosuccinate, disodium cocamido PEG-3 sulfosuccinate, disodium cocaminopropyl iminodiacetate, disodium cocoamphocarboxyethylhydroxypropylsulfonate, disodium cocoamphodiacetate, disodium cocoamphodipropionate, disodium coco-polyglucose citrate, disodium cocopolyglucose sulfosuccinate, disodium cocoyl butyl glucefh-10 sulfosuccinate, disodium cocoyl glutamate, disodium deceth-5 sulfosuccinate, disodium deceth-6 sulfosuccinate, disodium dicarboxyethyl cocopropylenediamine, disodium dihydroxyethyl sulfosuccinylundecylenate, disodium dimethicone copolyol sulfosuccinate, disodium distyrylbiphenyl disulfonate, disodium hydrogenated cottonseed glyceride sulfosuccinate, disodium hydrogenated tallow glutamate, disodium hydroxydecyl sorbitol citrate, disodium isodecyl sulfosuccinate, disodium isostearamido MEA-sulfosuccinate, disodium isostearamido MIPA-sulfosuccinate, disodium isostearoamphodiacetate, disodium isostearoamphodipropionate, disodium isostearyl sulfosuccinate, disodium laneth-5 sulfosuccinate, disodium lauramido MEA-sulfosuccinate, disodium lauramido PEG-2 sulfosuccinate, disodium lauramido PEG-5 sulfosuccinate, disodium laureth sulfosuccinate, disodium laureth-12 sulfosuccinate, disodium laureth-5 carboxyamphodiacetate, disodium laureth-6 sulfosuccinate, disodium laureth-7 citrate, disodium laureth-9 sulfosuccinate, disodium lauriminodipropionate, disodium lauroamphodiacetate, disodium lauroamphodipropionate, disodium lauryl sulfosuccinate, disodium myristamido MEA-sulfosuccinate, disodium nonoxynol-10 sulfosuccinate, disodium oleamido MEA-sulfosuccinate, disodium oleamido MIPA-sulfosuccinate, disodium oleamido PEG-2 sulfosuccinate, disodium oleoamphodipropionate, disodium oleth-3 sulfosuccinate, disodium oleyl sulfosuccinate, disodium palmitamido PEG-2 sulfosuccinate, disodium palmitoleamido PEG-2 sulfosuccinate, disodium PEG-10 laurylcitrate sulfosuccinate, disodium PEG-4 cocamido MIPA-sulfosuccinate, disodium PEG-8 glyceryl caprylate/caprate, disodium PEG-8 ricinosuccinate, disodium PPG-2-isodeceth-7 carboxyamphodiacetate, disodium ricinoleamido MEA-sulfosuccinate, disodium sitostereth-14 sulfosuccinate, disodium stearamido MEA-sulfosuccinate, disodium steariminodipropionate, disodium stearoamphodiacetate, disodium stearyl sulfosuccinamate, disodium stearyl sulfosuccinate, disodium succinate, disodium succinoyl glycyrrhetinate, disodium tallamido MEA-sulfosuccinate, disodium tallow sulfosuccinamate, disodium tallow amido MEAsulfosuccinate, disodium tallow amphodiacetate, disodium tallow iminodipropionate, disodium tetrapropenyl succinate, disodium tridecylsulfosuccinate, disodium undecylenamido MEA-sulfosuccinate, disodium undecylenamido PEG-2 sulfosuccinate, disodium wheat germamido MEA-sulfosuccinate, disodium wheat germamido PEG-2 sulfosuccinate, disodium wheat germ amphodiacetate, disoyadimonium chloride, disteareth-2 lauroyl glutamate, disteareth-5 lauroyl glutamate, disteareth-6 dimonium chloride, ditallowamidoethyl hydroxypropylamine, ditallowedimonium chloride, diTEA-oleamido PEG-2 sulfosuccinate, di-TEA-palmitoyl aspartate, ditridecyl sodium sulfosuccinate, dodecylbenzene sulfonic acid, dodecylbenzyltrimonium chloride, dodecylxylyldtrimonium chloride, dodoxynol-12, dodoxynol-5, dodoxynol-6, dodoxynol-7, dodoxynol-9, erucamidopropyl hydroxysultaine, ethyl butylacetylaminopropionate, ethyl guiazulene sulfonate, ethyl PEG-15 cocamine sulfate, glycol stearate, hexeth-4 carboxylic acid, hydrogenated castor oil, hydrogenated coconut acid, hydrogenated ditallowamine, hydrogenated menhaden acid, hydrogenated tallow amide, hydrogenated tallow betaine, hydrogenated tallowamide DEA, hydrogenated tallowamine, hydrogenated tallowamine oxide, hydrogenated tallowtrimonium chloride, hydrolyzed beeswax, hydroxyceteth-60, hydroxyethyl carboxymethyl cocamidopropylamine, hydroxyethyl cetyldimonium chloride, hydroxyethyl cetyldimonium phosphate, hydroxyethyl hydroxypropyl C12-15 alkoxypropylamine oxide, hydroxy ethylbutylamine laureth sulfate, isoceteth-30, isopropanolamine lanolate, isopropyl hydroxycetyl ether, isopropylamine dodecylbenzenesulfonate, isostearamidomorpholine stearate, isostearamidopropyl betaine, isostearamidopropyl morpholine oxide, isostearamidopropylamine oxide, isosteareth11 carboxylic acid, isosteareth-50, isosteareth-6 carboxylic acid, isostearic acid, isostearoyl hydrolyzed collagen, laneth40, laneth-50, laneth-75, lanolinamide DEA, lauramide/myristamide DEA, lauramidopropyl betaine, lauramidopropylamine oxide, lauramine oxide, laureth-1, laureth-10, laureth-10 carboxylic acid, laureth-11 carboxylic acid, laureth-13 carboxylic acid, laureth-14 carboxylic acid, laureth17 carboxylic acid, laureth-2, laureth-20, laureth-23, laureth25, laureth-3, laureth-3 carboxylic acid, laureth-3 phosphate, laureth-30, laureth-4, laureth-4 carboxylic acid, laureth-40, laureth-5, laureth-5 carboxylic acid, laureth-6, laureth-6 carboxylic acid, laureth-6 citrate, laureth-7, laureth-7 citrate, laureth-7 tartrate, laureth-8 phosphate, lauroamphodipropionic acid, lauroyl hydrolyzed collagen, lauroyl sarcosine, lauryl betaine, lauryl hydroxysultaine, lauryl isoquinolinium bromide, lauryl polyglucose, lauryl pyrrolidone, lauryl sultaine, laurylpyridinium chloride, lysine thiazolidine carboxylate, magnesium cocoate, magnesium coco-sulfate, magnesium lanolate, magnesium laureth sulfate, magnesium laureth-11 carboxylate, magnesium laureth-16 sulfate, magnesium laureth-5 sulfate, magnesium laureth-8 sulfate, magnesium lauryl hydroxypropyl sulfonate, magnesium lauryl sulfate, magnesium myreth sulfate, magnesium oleth sulfate, magnesium PEG-3 cocamide sulfate, magnesium tallowate, mannitan oleate, MEA-dicetearyl phosphate, MEA-laureth sulfate, MEA-laureth-6 carboxylate, MEA-lauryl sulfate, MEA-PPG-6-laureth-7-carboxylate, meroxapol 105, meroxapol 108, meroxapol 171, meroxapol 172, meroxapol 174, meroxapol 178, meroxapol 251, meroxapol 252, meroxapol 254, meroxapol 255, meroxapol 258, meroxapol 311, meroxapol 312, meroxapol 314, methoxy-PEG-7 rutinyl succinate, methyl morpholine oxide, methylpyrrolidone, methylbenzethonium chloride, minkamide DEA, minkamidopropyl betaine, minkamidopropyl dimethylamine, minkamidopropylamine oxide, MIPA C12-15 pareth sulfate, MIPA-dodecylbenzenesulfonate, MIPA-laureth sulfate, MIPA-lauryl sulfate, mixed isopropanolamines lanolate, mixed isopropanolamines lauryl sulfate, mixed isopropanolamines myristate, myreth-2 myristate, myreth-3 carboxylic acid, myreth-3 myristate, myreth-5 carboxylic acid, myristamidopropyl betaine, myristamidopropyl dimethylamine dimethicone copolyol phosphate, myristamidopropyl dimethylamine phosphate, myristamidopropylamine oxide, myristamine oxide, myristaminopropionic acid, myristoyl hydrolyzed collagen, myristoyl sarcosine, myristyl/cetyl amine oxide, myristyl betaine, noneth-8, nonoxynol-10 carboxylic acid, nonoxynol-10 phosphate, nonoxynol-100, nonoxynol-11, nonoxynol-12, nonoxynol-13, nonoxynol-14, nonoxynol-15, nonoxynol-18, nonoxynol-2, nonoxynol-20, nonoxynol-23, nonoxynol-30, nonoxynol-4, nonoxynol-40, nonoxynol-44, nonoxynol-5, nonoxynol-5 carboxylic acid, nonoxynol-50, nonoxynol-6, nonoxynol-6 phosphate, nonoxynol-7, nonoxynol-8, nonoxynol-8 carboxylic acid, nonoxynol-9, nonoxynol-9 phosphate, nonyl nonoxynol-10, nonyl nonoxynol-10 phosphate, nonyl nonoxynol-100, nonyl nonoxynol-15 phosphate, nonyl nonoxynol-150, nonyl nonoxynol-24 phosphate, nonyl nonoxynol-49, nonyl nonoxynol-7 phosphate, nonyl nonoxynol-9 phosphate, octeth-3 carboxylic acid, octoxynol-1, octoxynol-10, octoxynol-11, octoxynol-13, octoxynol-16, octoxynol-20 carboxylic acid, octoxynol-3, octoxynol-30, octoxynol-40, octoxynol-5, octoxynol-7, octoxynol-70, octoxynol-8, octoxynol-9, octoxynol-9 carboxylic acid, oleamidopropyl betaine, oleamidopropyl hydroxysultaine, oleamidopropylamine oxide, oleamine oxide, oleoyl hydrolyzed collagen, oleoyl sarcosine, oleth-10, oleth-10 carboxylic acid, oleth-10 phosphate, oleth12, oleth-15, oleth-16, oleth-2, oleth-20, oleth-20 phosphate, oleth-23, oleth-25, oleth-3 carboxylic acid, oleth-3 phosphate, oleth-4 phosphate, oleth-44, oleth-5 phosphate, oleth 50, oleth-6 carboxylic acid, oleyl betaine, olivamide DEA, olivamidopropyl betaine, olivamidopropylamine oxide, olive oil PEG-10 esters, palm kernelamide DEA, palm kernelamide MEA, palm kernelamide MIPA, palm kernelamidopropyl betaine, palmamide DEA, palmamide MEA, palmamide MIPA, palmamidopropyl betaine, palmitamidopropyl betaine, palmitamidopropylamine oxide, palmitamine oxide, palmitoyl hydrolyzed collagen, palmitoyl hydrolyzed wheat protein, pea ethyl cocoyl arginate, peanutamide MEA, peanutamide MIPA, PEG/PPG-300/55 copolymer, PEG-10 castor oil, PEG-10 cocamine, PEG-10 coco-benzonium chloride, PEG-10 isostearate, PEG-10 soyamine, PEG-10 stearate, PEG-10 stearyl benzonium chloride, PEG-100 castor oil, PEG-100 hydrogenated castor oil, PEG-100 lanolin, PEG-100 stearate, PEG-11 cocamide, PEG-120 glyceryl stearate, PEG-120 stearate, PEG-15 castor oil, PEG-15 cocamine, PEG-15 cocomonium chloride, PEG-15 hydrogenated tallow amine, PEG-15 oleammonium chloride, PEG-15 soyamine, PEG-15 stearmonium chloride, PEG-150 distearate, PEG-150 laurate, PEG-150 oleate, PEG-150 stearate, PEG-16 hydrogenated castor oil, PEG-175 distearate, PEG-2 castor oil, PEG-2 coco-benzonium chloride, PEG-2 cocomonium chloride, PEG-2 hydrogenated tallow amine, PEG-2 oleammonium chloride, PEG-2 sorbitan isostearate, PEG-2 soyamine, PEG-2 stearamide carboxylic acid, PEG-20 castor oil, PEG-20 cocamine, PEG-20 glyceryl isostearate, PEG-20 hydrogenated castor oil, PEG-20 hydrogenated tallow amine, PEG-20 laurate, PEG-20 myristate, PEG-20 oleate, PEG-20 palmitate, PEG-20 sorbitan beeswax, PEG-20 sorbitan isostearate, PEG-20 stearate, PEG-20 tallate, PEG-200 castor oil, PEG-200 glyceryl stearate, PEG-200 glyceryl tallowate, PEG-200 hydrogenated castor oil, PEG-200 trihydroxystearin, PEG-23 oleate, PEG-25 castor oil, PEG-25 diethylmonium chloride, PEG-25 glyceryl stearate, PEG-25 hydrogenated castor oil, PEG-28 glyceryl tallowate, PEG-29 castor oil, PEG-3 castor oil, PEG-3 cocamide, PEG-3 lauramine oxide, PEG-3 oleamide, PEG-30 castor oil, PEG-30 glyceryl cocoate, PEG-30 glyceryl isostearate, PEG-30 glyceryl oleate, PEG-30 glyceryl stearate, PEG-30 hydrogenated castor oil, PEG-30 hydrogenated tallow amine, PEG-30 oleamine, PEG-30 stearate, PEG-32 laurate, PEG-32 oleate, PEG-32 stearate, PEG-33 castor oil, PEG-35 castor oil, PEG-35 hydrogenated castor oil, PEG-35 stearate, PEG-36 castor oil, PEG-36 oleate, PEG-36 stearate, PEG-4 castor oil, PEG-4 laurate, PEG-4 stearamide, PEG-40 castor oil, PEG-40 hydrogenated castor oil, PEG-40 hydrogenated tallow amine, PEG-40 sorbitan diisostearate, PEG-40 sorbitan perisostearate, PEG-40 sorbitan peroleate, PEG-40 sorbitan stearate, PEG-40 sorbitol hexaoleate, PEG-40 stearate, PEG-44 sorbitan laurate, PEG-45 hydrogenated castor oil, PEG-45 stearate, PEG-45 stearate phosphate, PEG-4-PPG-7 C13/C15 alcohol, PEG-5 castor oil, PEG-5 cocamide, PEG-5 ditridecylmonium chloride, PEG-5 glyceryl stearate, PEG-5 hydrogenated castor oil, PEG-5 hydrogenated corn glycerides, PEG-5 soyamine, PEG-5 stearate, PEG-5 stearyl ammonium chloride, PEG-5 stearyl ammonium lactate, PEG-5 tallow benzonium chloride, PEG-50 castor oil, PEG-50 hydrogenated castor oil, PEG-50 stearamine, PEG-50 stearate, PEG-6 cocamide, PEG-6 oleate, PEG-6 palmitate, PEG-6 sorbitan beeswax, PEG-60 castor oil, PEG-60 glyceryl isostearate, PEG-60 hydrogenated castor oil, PEG-60 sorbitan stearate, PEG-66 trihydroxystearin, PEG-7 cocamide, PEG-7 glyceryl cocoate, PEG-7 hydrogenated castor oil, PEG-7 oleate, PEG75 castor oil, PEG-75 dioleate, PEG-75 lanolin, PEG-75 lanolin oil, PEG-75 lanolin wax, PEG-75 laurate, PEG-75 oleate, PEG-75 sorbitan laurate, PEG-75 stearate, PEG-78 glyceryl cocoate, PEG-8 castor oil, PEG-8 laurate, PEG-8 propylene glycol cocoate, PEG-8 ricinoleate, PEG-8 sorbitan beeswax, PEG-8 soyamine, PEG-8 stearate, PEG-80 glyceryl cocoate, PEG-80 hydrogenated castor oil, PEG-80 jojoba acid, PEG-80 jojoba alcohol, PEG-80 sorbitan laurate, PEG80 sorbitan palmitate, PEG-85 lanolin, PEG-9 castor oil, PEG-9 ricinoleate, PEG-90 stearate, pentaerythrityl tetraisostearate, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, polyglyceryl-4-PEG-2 cocamide, polysorbate 20, polysorbate 40, polysorbate 60, polysorbate 65, polysorbate 80, polysorbate 85, potassium abietoyl hydrolyzed collagen, potassium C9-15 alkyl phosphate, potassium castorate, potassium cetyl phosphate, potassium cocoate, potassium cocoyl glutamate, potassium cocoyl hydrolyzed collagen, potassium cornate, potassium cyclocarboxypropyloleate, potassium dihydroxyethyl cocamine oxide phosphate, potassium dodecylbenzenesulfonate, potassium laurate, potassium lauroyl collagen amino acids, potassium lauroyl hydrolyzed •collagen, potassium lauroyl hydrolyzed soy protein, potassium lauryl hydroxypropyl sulfonate, potassium lauryl sulfate, potassium methyl cocoyl taurate, potassium myristate, potassium myristoyl hydrolyzed collagen, potassium octoxynol-12 phosphate, potassium oleate, potassium oleoyl hydrolyzed collagen, potassium olivate, potassium palmitate, potassium ricinoleate, potassium stearate, potassium stearoyl hydrolyzed collagen, potassium tallowate, potassium toluenesulfonate, potassium undecylenoyl hydrolyzed collagen, potassium xylene sulfonate, PPG-10 cetyl ether, PPG-10 cetyl ether phosphate, PPG-15-PEG-11 hydrogenated lauryl alcohol ether, PPG-17 butyl ether, PPG-20 butyl ether, PPG24 butyl ether, PPG-25 diethylmonium chloride, PPG-3 hydrogenated castor oil, PPG-30-buteth-30, PPG-4 laureth-5, PPG-40 diethylmonium chloride, PPG-50 cetyl ether, PPG5-ceteth-10 phosphate, PPG-5-ceteth-20, PPG-8-ceteth-10, PPG-8-ceteth-20, PPG-9 diethylmonium chloride, propylene glycol soyate, quaternium-14, quaternium-18, quaternium24, quaternium-52, raffinose oleate, rapeseedamidopropyl benzyldimonium chloride, ricinoleamidopropyl betaine, ricinoleth-40, saponins, sesamide DEA, sesamidopropyl betaine, sesamidopropyl dimethylamine, sesamidopropylamine oxide, sodium/MEA laureth-2 sulfosuccinate, sodium/TEA-lauroyl collagen amino acids, sodium/TEAlauroyl hydrolyzed collagen, sodium/TEA-lauroyl hydrolyzed keratin, sodium/TEA-lauroyl keratin amino acids, sodium/TEA-undecylenoyl collagen amino acids, sodium/TEA-undecylenoyl hydrolyzed collagen, sodium behenoyl lactylate, sodium bisglycol ricinosulfosuccinate, sodium butoxynol-12 sulfate, sodium CI 1-15 pareth-7 carboxylate, sodium C12-13 pareth sulfate, sodium C12-14 olefin sulfonate, sodium C12-15 alkoxypropyl iminodipropionate, sodium C12-15 alkyl sulfate, sodium C12-15 pareth sulfate, sodium C12-15 pareth-15 sulfonate, sodium CI2-15 pareth-3 sulfonate, sodiumC12-15 pareth-6 carboxylate, sodiumC1215 pareth-7 carboxylate, sodium C12-15 pareth-7 sulfonate, sodium C12-18 alkyl sulfate, sodium C13-17 alkane sulfonate, sodium C14-16 olefin sulfonate, sodiumC14-17 alkyl sec sulfonate, sodium C14-18 olefin sulfonate, sodium C1618 olefin sulfonate, sodium CI6-20 alkyl sulfate, sodium C8-16 isoalkylsuccinyl lactoglobulin sulfonate, sodium C9-22 alkyl sec sulfonate, sodium caproamphoacetate, sodium caproamphohydroxypropylsulfonate, sodium caproamphopropionate, sodium caprylate, sodium capryleth-2 carboxylate, sodium capryleth-9 carboxylate, sodium capryloamphoacetate, sodium capryloamphohydroxypropylsulfonate, sodium capryloamphopropionate, sodium caprylyl sulfonate, sodium carboxyethyl tallow polypropylamine, sodium carboxymethyl cocopolypropylamine, sodium carboxymethyl oleyl polypropylamine, sodium carboxymethyl tallow polypropylamine, sodium castorate, sodium cetearyl sulfate, sodium ceteth-13 carboxylate, sodium cetyl sulfate, sodium cocaminopropionate, sodium coceth sulfate, sodium coco/hydrogenated tallow sulfate, sodium cocoamphoacetate, sodium cocoamphohydroxypropylsulfonate, sodium cocoamphopropionate, sodium cocoate, sodium cocoglyceryl ether sulfonate, sodium cocomonoglyceride sulfate, sodium cocomonoglyceride sulfonate, sodium cocopolyglucose tartrate, sodium coco-sulfate, sodium cocoyl collagen amino acids, sodium cocoyl glutamate, sodium cocoyl hydrolyzed collagen, sodium cocoyl hydrolyzed keratin, sodium cocoyl hydrolyzed rice protein, sodium cocoyl hydrolyzed soy protein, sodium cocoyl hydrolyzed wheat protein, sodium cocoyl isethionate, sodium cocoyl lactylate, sodium cocoyl sarcosinate, sodium comamphopropionate, sodium cumenesulfonate, sodium cyclopentane carboxylate, sodium deceth sulfate, sodium deceth-2 carboxylate, sodium decylbenzenesulfonate, sodium dicarboxyethylcoco phosphoethyl imidazoline, sodium diethylaminopropyl cocoaspartamide, sodium dihydroxycetyl phosphate, sodium dilaureth-7 citrate, sodium dodecylbenzenesulfonate, sodium ethyl 2-sulfolaurate, sodium glycereth-1 polyphosphate, sodium glyceryl oleate phosphate, sodium guiazulene sulfonate, sodium hydrogenated tallow glutamate, sodium isostearoamphoacetate, sodium isostearoamphopropionate, sodium laneth sulfate, sodium lauramido diacetate, sodium lauramidopropyl hydroxyphostaine, sodium lauraminopropionate, sodium laurate, sodium laureth sulfate, sodium laureth-11 carboxylate, sodium laureth-12 sulfate, sodium laureth-13 carboxylate, sodium laureth-14 carboxylate, sodium laureth-17 carboxylate, sodium laureth-4 carboxylate, sodium laureth-4 phosphate, sodium laureth-5 carboxylate, sodium laureth-5 sulfate, sodium laureth-6 carboxylate, sodium laureth-7 sulfate, sodium laureth-7 tartrate, sodium laureth-8 sulfate, sodium lauriminodipropionate, sodium lauroampho PG-acetate phosphate, sodium lauroamphoacetate, sodium lauroamphohydroxypropylsulfonate, sodium lauroyl aspartate, sodium lauroyl glutamate, sodium lauroyl hydrolyzed collagen, sodium lauroyl isethionate, sodium lauroyl methylaminopropionate, sodium lauroyl sarcosinate, sodium lauroyl taurate, sodium lauryl phosphate, sodium lauryl sulfate, sodium lauryl sulfoacetate, sodium lignosulfonate, sodium methyl 2-sulfolaurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, sodium methylnaphthalenesulfonate, sodium myreth sulfate, sodium myristate, sodium myristoamphoacetate, sodium myristoyl glutamate, sodium myristoyl isethionate, sodium myristoyl sarcosinate, sodium myristyl sulfate, sodium nonoxynol-1 sulfate, sodium nonoxynol-10 sulfate, sodium nonoxynol-4 sulfate, sodium nonoxynol-6 phosphate, sodium nonoxynol-9 phosphate, sodium octoxynol-2 ethane sulfonate, sodium octyl sulfate, sodium oleate, sodium oleoamphoacetate, sodium oleoamphohydroxypropylsulfonate, sodium oleoamphopropionate, sodium oleoyl isethionate, sodium oleth-7 phosphate, sodium oleth-8 phosphate, sodium olivate, sodium palm kernelate, sodium palmate, sodium palmitate, sodium PEG-6 cocamide carboxylate, sodium polydimethylglycinophenolsulfonate, sodium polynaphthalenesulfonate, sodium polystyrene sulfonate, sodium ricinoleoamphoacetate, sodium shale oil sulfonate, sodium soya hydrolyzed collagen, sodium stearate, sodium stearoamphoacetate, sodium stearoamphopropionate, sodium stearyl betaine, sodium stearyl sulfate, sodium tallamphopropionate, sodium tallow sulfate, sodium tallowamphoacetate, sodium tallowate, sodium toluenesulfonate, sodium trideceth sulfate, sodium trideceth-12 carboxylate, sodium trideceth-3 carboxylate, sodium trideceth-6 carboxylate, sodium trideceth-7 carboxylate, sodium trideceth-8 carboxylate, sodium tridecyl sulfate, sodium tridecylbenzenesulfonate, sodium trilaureth-4 phosphate, sodium undecylenoamphoacetate, sodium undecylenoamphopropionate, sodium wheat germamphoacetate, sodium xylenesulfonate, soya hydroxyethyl imidazoline, soyamide DEA, soyamidopropyl betaine, soyamidopropyl dimethylamine, soyamidopropyl ethyldimonium ethosulfate, soytrimonium chloride, stearamidopropyl betaine, stearamidopropyl dimethylamine, stearamidopropylamine oxide, stearamine oxide, steareth-10, steareth-100, steareth-2, steareth-20, steareth21, steareth-25, steareth-27, steareth-30, steareth-40, steareth-50, stearoyl sarcosine, stearyl betaine, sucrose laurate, sucrose palmitate, sulfated castor oil, sulfated glyceryl oleate, sulfated olive oil, sulfated peanut oil, sulfonated castor oil, tallow amide, tallow amine, tallow betaine, tallow dihydroxyethyl betaine, tallow hydroxyethyl imidazoline, tallowalkonium chloride, tallowamidopropyl betaine, tallowamidopropyl dimethylamine, tallowamidopropyl hydroxysultaine, tallowamidopropylamine oxide, tallowamine oxide, tallowedimonium propyltrimonium dichloride, tallowtrimonium chloride, TEA-abietoyl hydrolyzed collagen, TEA-C 10-12 alkyl sulfate, TEA-C 10-14 alkyl benzenesulfonate, TEA-C 10-15 alkyl sulfate, TEA-C12-15 alkyl sulfate, TEA-cocoate, TEA-coco-sulfate, TEA-cocoyl glutamate, TEA-cocoyl hydrolyzed collagen, TEA-cocoyl sarcosinate, TEAdodecylbenzenesulfonate, TEA-hydrogenated tallow glutamate, TEA-isostearate, TEA-i so stearoyl hydrolyzed collagen, TEA-lauraminopropionate, TEA-laureth sulfate, TEA-lauroyl collagen amino acids, TEA-lauroyl glutamate, TEA-lauroyl hydrolyzed collagen, TEA-lauroyl keratin amino acids, TEA-lauroyl lactylate, TEA-lauroyl sarcosinate, TEA-lauryl sulfate, TEA-myristaminopropionate, TEA-myristate, TEA-myristoyl hydrolyzed collagen, TEA-oleate, TEA-oleoyl hydrolyzed collagen, TEA-oleoyl sarcosinate, TEA-oleyl sulfate, TEA-palm kernel sarcosinate, TEA-palmitate, TEA-PEG-3 cocamide sulfate, TEA-stearate, TEA-tallate, TEA-tridecylbenzenesulfonate, TEA-undecylenoyl hydrolyzed collagen, tetrasodium dicarboxyethyl stearyl sulfosuccinamate, TIPA-laureth sulfate, TIPA-lauryl sulfate, TIPA-stearate, tocophereth-10, tocophereth-12, tocophereth-18, tocophereth-5, tocophereth-50, toluene sulfonic acid, triceteareth-4 phosphate, triceteth-5 phosphate, trideceth-12, trideceth-15 carboxylic acid, trideceth-19 carboxylic acid, trideceth-3 carboxylic acid, trideceth-4 carboxylic acid, trideceth-6, trideceth-6 phosphate, trideceth-7 carboxylic acid, trideceth-8, tridecylbenzenesulfonic acid, triheptanoin, trilauryl phosphate, triolein PEG-6 esters, trisodium lauroampho PG-acetate phosphate chloride, tristearyl phosphate, undecyl polyglucose, undecylenamidopropyl betaine, undecylenamidopropylamine oxide, undecylenoyl wheat amino acids, wheat germamide DEA, wheat germamidopropyl betaine, wheat germamidopropyl dimethylamine, wheat germamidopropyl dimethylamine lactate, wheat germamidopropylamine oxide, xylene sulfonic acid, and zinc pentadecene tricarboxylate.

Emollients. A further ingredient of the exemplary styling compositions are one or more emollients. As defined herein, an "emollient" is a material that protects against wetness or irritation, softens, soothes, supples, coats, lubricates, moisturizes, protects and/or cleanses the skin. Suitable emollients comprise one or more of: a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, cetearyl isononanoate and/or cetyl palmitate. The emollient generally comprises from about 0.5% to about 15% and optionally about 1% to about 10% by weight or more of the hair styling compositions.

Emulsifiers. The styling formulations may also comprise one or more emulsifiers. Suitable emulsifiers comprise a copolymer of an unsaturated ester and styrene sulphonate monomer, cetearyl alcohol, glyceryl ester, polyoxy ethylene glycol ether of cetearyl alcohol, stearic acid, polysorbate-20, ceteareth-20, lecithin, glycol stearate, polysorbate-60 and/or polysorbate-80. The emulsifier(s) generally comprises from about 0.05-15% by weight and optionally from about 0.1-10% by weight or more of the styling formulations.

Preservatives. One or more preservatives may be included in the hair styling compositions. Examples of such preservatives include one or more glycerin containing compound (e.g., glycerin or ethylhexylglycerin or phenoxyethanol), benzyl alcohol, EDTA, potassium sorbate and/or grapefruit seed extract. The preservative(s) generally comprises from about 0.1-5% by weight and optionally from about 0.3-3% by weight of the hair styling compositions. In another example embodiment, the hair styling compositions are paraben free. The preservative(s) generally comprises from 0.05-15% by weight and optionally from about 0.1-10% by weight or more of the hair styling compositions.

Skin Protecting Agents. The hair styling compositions comprise one or more skin protecting agents. Skin protecting agents comprise one or more agents that prevent the transmission of microbes (e.g., include antibacterial agents), skin cleansing agents (e.g. disinfectants and antiseptic agents) and sunscreen agents. Skin cleansing agents used in the hair styling compositions comprise sodium cocyl amino acids, benzalkonium chloride and/or centrimonium chloride. The skin protecting agent(s) generally comprises from about 0.1-10% by weight or more or more and optionally from about 0.5-5% by weight of the formulations.

Diluents. The term "diluent" as used herein refers to substances that may be used to dilute the active ingredient, the keratin protein fraction and keratin cross-linking agent. Water is an acceptable diluent. The formulations require use of greater than 1% water to be effective. Advantageously, greater than five percent water is used, and optionally, greater than 50%, and even optionally, greater than 80% water is used. Alcohols such as ethyl alcohol and isopropyl alcohol may be used at low concentrations (about 0.5%) to enhance shaft penetration and reduce odor. High concentrations (about 35% and greater) of alcohols are not suitable as they disrupt the effectiveness of the formulations.

Auxiliary Ingredients. The hair styling compositions also comprise one or more thickeners, particularly, when the formulation is in the form of a cream, lotion, mask or gel. Such thickeners comprise polyethylene glycol and/or sodium polyacrylate. The thickeners may be present in an amount of about 0.1-5% by weight and optionally in the amount of about 0.2-1% by weight.

Fragrances may also be added to mask the odor of various other components in the formulation of example embodiments. Examples of such fragrances include but are not limited to caramel, vanilla. The thickener(s) may be present in an amount of about 0.1-10% by weight or more and optionally in the amount of about 0.5-5% by weight.

The hair styling compositions may also contain conventional cosmetic hair conditioning ingredients, botanical products, and other optional cosmetic ingredients, additives, products or materials, and cosmetic adjuvants, well known in the hair care and personal care formulation arts, such as an auxiliary hair protectant, heat protective ingredient, such as a silicone or silicone derivative.

A non-exhaustive list of constituents that may be contained in exemplary styling compositions include those listed in Table 1:

TABLE 1

| CONSTITUENT (INCI Name) | Other Chemical Name |
| --- | --- |
| 2-AMINOBUTANOL | 2-aminobutan-1-ol |
| 2-BROMO-2-NITRO-PROPANE-1,3-DIOL | Bronopol |
| 2-NITRO-p-PHENYLENE-DIAMINE | 2-nitro-p-phenylenediamine (CI 76070) |
| 2-OLEAMIDO-1,3-OCTA-DECANEDIOL | 1,3-octadecanediol, 2-oleamido- |
| *ACER SACCHARINUM* | Extractives and their physically modified derivatives such as tinctures, concretes, absolutes, essential oils, oleoresins, terpenes, terpene-free fractions, distillates, residues, etc., obtained from *Acer saccharinum* |
| ACETAMIDE MEA | N-2-hydroxyethylacetamide |
| ACETYLATED LANOLIN | Lanolin, acetate |
| ACETYLATED LANOLIN ALCOHOL | Acetic acid, esters with lanolin alcs |
| *ACHILLEA MILLEFOLIUM* | Yarrow, *Achillea millefolium*, ext. Extractives and their physically modified derivatives such as tinctures, concretes, absolutes, essential oils, oleoresins, terpenes, terpene-free fractions, distillates, residues, etc., obtained from *Achillea millefoliu* |
| ACRYLATES/ACRYLA-MIDE COPOLYMER | Propenamide, polymer with propenoic acid, butenoic acid, and/or alkyl propenoates |
| ACRYLATES/C10-30 ALKYL | C10-C30 alkyl propenoate, polymer with propenoic |

TABLE 1-continued

| CONSTITUENT (INCI Name) | Other Chemical Name |
|---|---|
| ACRYLATE CROSSPOLYMER | acid, butenoic acid and/or alkyl propenoates, product with propenyl sucrose ether or propenyl 2,2-dihydroxymethyl-1,3-propanediol |
| ACRYLATES/DIMETHICONE COPOLYMER | |
| ACRYLATES/PVP COPOLYMER | 2-propenoic acid, 2-methyl-, polymer with 1-ethenyl-2-pyrrolidinone and ethyl 2-methyl-2-propenoate |
| ACRYLATES/STEARETH-20 METHACRYLATE COPOLYMER | Stearyl alcohol, product with oxirane, butenoate ester, polymer with propenoic acid, butenoic acid, and/or alkyl propenoates |
| ACRYLATES/t-BUTYL-ACRYLAMIDE COPOLYMER | |
| ACRYLATES COPOLYMER | 2-propenoic acid, 2-methyl-, polymer with ethyl 2-propenoate and methyl 2-methyl-2-propenoate |
| *ACTINIDIA CHINENSIS* | *Actinidia chinensis*, ext. Extractives and their physically modified derivatives such as tinctures, concretes, absolutes, essential oils, oleoresins, terpenes, terpene-free fractions, distillates, residues, etc., obtained from *Actinidia chinensis*, Actinid |
| *AESCULUS HIPPOCASTANUM* | Horse chestnut, *Aesculus hippocastanum*, ext. Extractives and their physically modified derivatives such as tinctures, concretes, absolutes, essential oils, oleoresins, terpenes, terpene-free fractions, distillates, residues, etc., obtained from *Aesculus* |
| ALANINE | L-alanine, DL-alanine |
| ALGAE | |
| ALLANTOIN | Allantoin |
| *ALOE BARBADENSIS* | *Aloe vera*, ext. Extractives and their physically modified derivatives such as tinctures, concretes, absolutes, essential oils, oleoresins, terpenes, terpene-free fractions, distillates, residues, etc., obtained from *Aloe vera*, Liliaceae |
| *ALTHEA OFFICINALIS* | Marshmallow (*Althaea officinalis*), ext. Extractives and their physically modified derivatives such as tinctures; concretes, absolutes, essential oils, oleoresins, terpenes, terpene-free fractions, distillates, residues, etc., obtained from *Althaea offici* |
| ALUMINUMDISTEARATE | Hydroxyaluminium distearate |
| AMINOMETHYL PROPANOL | 2-amino-2-methylpropanol |
| AMMONIUM BENZOATE 1863-63-4 | Ammonium benzoate |
| AMMONIUM HYDROXIDE | Ammonia, aqueous solution |
| AMMONIUM LAURYL SULFATE | Ammonium dodecyl sulphate |
| AMODIMETHICONE | |
| AMODIMETHICONECETRIUM CHLORIDE | |
| AMP-ISOSTEAROYL HYDROLYZED WHEAT PROTEIN | Protein hydrolyzates, wheat gluten, isostearoyl-, product 2-amino-2-methylpropanol |
| *ANTHEMIS NOBILIS* | *Anthemis nobilis*, ext. Extractives and their physically modified derivatives such as tinctures, concretes, absolutes, essential oils, oleoresins, terpenes, terpene-free fractions, distillates, residues, etc., obtained from *Anthemis nobilis*, Compositae |
| AQUA | Water |
| ARGININE | Arginine, DL-arginine |
| ASCORBIC ACID | Ascorbic acid |
| BASIC BLUE 9 | Methylthioninium chloride (CI 52015) |
| BASIC BLUE 99 | 3-[(4-amino-6-bromo-5,8-dihydro-1-hydroxy-8-imino-5-oxo-2-naphtyl)amino]-N,N,N-trimethylanilinium chloride (CI 56059) |
| BASIC BROWN 16 | [8-[(p-aminophenyl)azo]-7-hydroxy-2-naphthyl]trimethylammonium chloride (CI 12250) |
| BASIC BROWN 17 | [8-[(4-amino-2-nitrophenyl)azo]-7-hydroxy-2-naphthyl]trimethylammonium chloride (CI 12251) |
| BASIC RED 2 | 3,7-diamino-2,8-dimethyl-5-phenyl-phenazinium chloride (CI 50240) |
| BASIC RED 76 | [7-hydroxy-8-[(2-methoxyphenyl)azo]-2-naphthyl]trimethylammonium chloride (CI 12245) |
| BASIC VIOLET 14 | (4-(4-aminophenyl)(4-iminocyclohexa-2,5-dienylidene)methyl)-2-methylanilinehydro-chloride(CI42510) |
| BASIC YELLOW 57 | 3-[(4,5-dihydro-3-methyl-5-oxo-1-phenyl-1H-pyrazol-4-yl)azo]-N,N,N-trimethylanilinium chloride (CI 12719) |
| BEESWAX ACID | Fatty acids, beeswax |
| BEHENTRIMONIUM CHLORIDE | Docosyltrimethylammonium chloride |
| BEHENTRIMONIUM METHOSULFATE | Docosyltrimethylammonium methyl sulphate |

TABLE 1-continued

| CONSTITUENT (INCI Name) | Other Chemical Name |
|---|---|
| BENZALKONIUM CHLORIDE | Quaternary ammonium compounds, benzyl-C8-18-alkyldimethyl, chlorides |
| BENZOIC ACID | Benzoic acid |
| BENZOPHENONE-2 | 2,2',4,4'-tetrahydroxybenzophenone |
| BENZOPHENONE-3 | Oxybenzone |
| BENZOPHENONE-4 | Sulisobenzone |
| BENZYL ALCOHOL | Benzyl alcohol |
| BERTHOLLETIA EXCELSA | |
| BETAINE | Betaine |
| BHA | Tert-butyl-4-methoxyphenol |
| BHT | 2,6-di-tert-butyl-P-cresol |
| BISABOLOL | (R*,R*)-a, 4-dimethyl-a-(4-methyl-3-pentenyl)cyclohex-3-ene-1-methanol |
| BUTANE | Butane |
| BUTYL ESTER OF ETHYLENE/MA COPOLYMER | |
| BUTYL ESTER OF PVM/MA COPOLYMER | 2-butenedioic acid (Z)-, polymer with methoxyethene, monobutyl ester |
| BUTYL METHOXYDI-BENZOYLMETHANE | 1-[4-(1,1-dimethylethyl)phenyl]-3-(4-methoxyphenyl)propane-1,3-dione |
| BUTYLENE GLYCOL | Butane-1,3-diol |
| BUTYLPARABEN | Butyl 4-hydroxybenzoate |
| BUXUS CHINENSIS | Jojoba, ext. Extractives and their physically modified derivatives such as tinctures, concretes, absolutes, essential oils, oleoresins, terpenes, terpene-free fractions, distillates, residues, etc., obtained from Simmondsia chinensis N., Buxaceae; Extrac |
| C12-15 ALKYL BENZOATE | Benzoic acid, C12-15-alkyl esters |
| C13-14 ISOPARAFFIN | Alkanes, iso-, C13-14 |
| C18-36 ACID GLYCOL ESTER | Fatty acids, C18-36, esters with ethylene glycol |
| C9-11 PARETH-8 | Alcohols, C9-11, ethoxylated |
| CALCIUM CARBONATE | Calcium carbonate |
| CALCIUM HYDROXIDE | Calcium dihydroxide |
| CALCIUM PANTOTHENATE | Calcium pantothenate, D-form; Calcium (.+−.)-N-(2,4-dihydroxy-3,3-dimethyl-1-oxobutyl)-á-alaninate |
| CALENDULA OFFICINALIS | Calendula officinalis, ext. Extractives and their physically modified derivatives such as tinctures, concretes, absolutes, essential oils, oleoresins, terpenes, terpene-free fractions, distillates, residues, etc., obtained from Calendula officinalis, Com |
| CAMELIA OLEIFERA | Extractives and their physically modified derivatives such as tinctures, concretes, absolutes, essential oils, oleoresins, terpenes, terpene-free fractions, distillates, residues, etc., obtained from Camelia oleifera |
| CAMELIA SINENSIS | Tea, ext. Extractives and their physically modified derivatives such as tinctures, concretes, absolutes, essential oils, oleoresins, terpenes, terpene-free fractions, distillates, residues, etc., obtained from Thea chinensis, Theaceae |
| CANANGA ODORATA | Ylang-ylang, ext. Extractives and their physically modified derivatives such as tinctures, concretes, absolutes, essential oils, oleoresins, terpenes, terpene-free fractions, distillates, residues, etc., obtained from Cananga odorata, Annonaceae |
| CANDELILLA CERA | Candelilla wax. The wax from Euphorbia antisiphylitica or Pedilanthus pavonis, Euphorbiaceae |
| CAPRYLIC/CAPRIC/STEARIC TRIGLYCERIDE | Octadecanoic acid, mixed triesters with octanoic acid, decanoic acid and 1,2,3-propanetriol |
| CAPRYLIC/CAPRIC TRIGLYCERIDE | Glycerides, mixed decanoyl and octanoyl |
| CAPRYLYL PYRROLIDONE | Pyrrolidone, N-octyl- |
| CARAMEL | Caramel (color). The substance obtained by controlled heat treatment of food-grade carbohydrates. Food-grade acids, alkalies, and salts may be used to assist carmelization. Food-grade antifoaming agents may be used in an amount not greater than that re |
| CARBOMER | Carbomer |
| CARBOMER 940 | |
| CARNAUBA | Carnauba wax. The wax derived from Copernicia cerifera, Palmae |
| CARTHAMUS TINCTORIUS | Safflower oil. Extractives and their physically modified derivatives. It consists primarily of the glycerides of the fatty acid linoleic. (Carthamus tinctorius, Compositae); Extractives and their physically modified derivatives such as tinctures, concrete |

TABLE 1-continued

| CONSTITUENT (INCI Name) | Other Chemical Name |
|---|---|
| CELETH-20 | |
| *CERA ALBA* | Beeswax. The wax obtained from the honeycomb of the bee. It consists primarily of myricyl palmitate, cerotic acid and esters and some high-carbon paraffins |
| CERA MICROCRISTALLINA | Paraffin waxes and Hydrocarbon waxes, microcryst.. A complex combination of long, branched chain hydrocarbons obtained from residual oils by solvent crystallization. It consists predominantly of saturated straight and branched chain hydrocarbons predomina |
| CERAMIDE 2 | |
| CERESIN | Ceresin. A complex combination of hydrocarbons produced by the purification of ozocerite with sulfuric acid and filtration through bone black to form waxy cakes |
| *CEREUS GRANDIFLORUS* | *Selenicereus grandiflorus*, ext. Extractives and their physically modified derivatives such as tinctures, concretes, absolutes, essential oils, oleoresins, terpenes, terpene-free fractions, distillates, residues, etc., obtained from *Selenicereus grandiflo* |
| CETEARETH-12 | |
| CETEARETH-20 | |
| CETEARETH-25 | |
| CETEARETH-30 | |
| CETEARETH-6 | |
| CETEARYL ALCOHOL | Alcohols, C16-18. This substance is identified by SDA Substance Name: C16-C18 alkyl alcohol and SDA Reporting Number: 19-060-00 |
| CETEARYL OCTANOATE | Hexanoic acid, 2-ethyl-, C16-18-alkyl esters |
| CETETH-20 | Poly(oxy-1,2-ethanediyl), a-hexadecyl-?-hydroxy- |
| CETRIMONIUM BROMIDE | Cetrimonium bromide |
| CETRIMONIUM CHLORIDE | Cetrimonium chloride |
| CETYL ACETATE | Hexadecyl acetate |
| CETYL ALCOHOL | Hexadecan-1-ol |
| *CHAMOMILLA RECUTITA* | *Matricaria recutita*, ext. Extractives and their physically modified derivatives such as tinctures, concretes, absolutes, essential oils, oleoresins, terpenes, terpene-free fractions, distillates, residues, etc., obtained from *Matricaria recutita*, Composi |
| CHITOSAN | Chitin, deacylated |
| CHITOSAN FORMATE | |
| CHITOSAN PCA | pyrrolidonecarboxylic acid salt |
| CHLOROACETAMIDE | 2-chloroacetamide |
| CHLORPHENESIN | Chlorphenesin |
| CHOLESTEROL | Cholesterol |
| CI 15510 | Sodium 4-[(2-hydroxy-1-naphthyl)azo]benzenesulphonate; Benzenesulfonic acid, 4-[(2-hydroxy-1-naphthalenyl)azo]-, Al-lake |
| CI 15985 | Disodium 6-hydroxy-5-[(4-sulphonato-phenyl)azo]naphthalene-2-sulphonate; Aluminum, 6-hydroxy-5-(4-sulfophenyl)azo2-naphthalenesulfonic acid complex. This substance is identified in the Colour Index by Colour Index Constitution Number, C.I. 159 |
| CI 16035 | Disodium 6-hydroxy-5-[(2-methoxy-4-sulphonato-m-tolyl)azo]naphthalene-2-sulphonate |
| CI 16185 | Trisodium 3-hydroxy-4-(4'-sulphonatonaphthylazo)naphthalene-2,7-disulphonate; Aluminum, 3-hydroxy-4-(4-sulfo-1-naphthalenyl)azo-2, 7-naphthalenedisulfonic acid complex. This substance is identified in the Colour Index by Colour Index Consti |
| CI 17200 | Disodium 5-amino-4-hydroxy-3-(phenylazo)naphthalene-2,7-disulphonate; 2,7-naphthalenedisulfonic acid, 5-amino-4-hydroxy-3-(3-phenylazo)-, Al-lake |
| CI 18050 | Disodium 5-acetylamino-4-hydroxy-3-(phenylazo)naphthalene-2,7-disulphonate |
| CI 19140 | Trisodium 5-hydroxy-1-(4-sulphophenyl)-4-(4-sulphophenylazo)pyrazole-3-carboxylate; Aluminum, 4,5-dihydro-5-oxo-1-(4-sulfo-phenyl)-4-(4-sulfophenyl)azo-1H-pyrazole-3-carboxylic acid complex. This substance is identified in the Colour |
| CI 42051 | Bis[hydrogen [4-[4-(diethylamino)-5'-hydroxy-2',4'-disulphonatobenzhydrylidene]cyclohexa-2,5-dien-1-ylidene]diethylammonium], calcium salt |
| CI 42090 | Diammonio(ethyl)[4-[[4-[ethyl(3-sulphonatobenzyl)amino]phenyl](2-sulphonatophenyl)methylene]cyclohexa-2,5-dien-1-ylidene](3-sulphonatobenzyl)ammonium; Dihydrogen (ethyl)[4-[4- |

TABLE 1-continued

| CONSTITUENT (INCI Name) | Other Chemical Name |
|---|---|
| | [ethyl(3-sulphonato-benzyl)]amino]-2'-sulphonato-benzhydrylidene]cy |
| CI 42520 | 4-[(4-amino-m-tolyl)(4-imino-3-methylcyclohexa-2,5-dien-1-ylidene)methyl]-o-toluidine monohydrochloride |
| CI 42600 | |
| CI 42735 | Hydrogen [4-[[4-(diethylamino)phenyl][4-[ethyl[(3-sulphonatobenzyl)amino]-o-tolyl]methylene]-3-methylcyclohexa-2,5-dien-1-ylidene](ethyl)(3-sulphonatobenzyl)ammonium, sodium salt |
| CI 47000 | 1,3-Isobenzofurandione, reaction products with methylquinoline and quinoline. This substance is identified in the Colour Index by Colour Index Constitution Number, C.I. 47000 |
| CI 47005 | Aluminum, 2-(1,3-dihydro-1,3-dioxo-2H-inden-2-ylidene)-1,2-dihydro-6,7-quinolin-edisulfonate complexes |
| CI 60725 | 1-hydroxy-4-(p-toluidino)anthraquinone |
| CI 60730 | Sodium 4-[(9,10-dihydro-4-hydroxy-9,10-dioxo-1-anthryl)amino]toluene-3-sulphonatecolorants |
| CI 61565 | 1,4-bis(p-tolylamino)anthraquinone |
| CI 61570 | Disodium 2,2'-(9,10-dioxoanthracene-1,4-diyldiimino)bis(5-methylsulphonate) |
| CI 69800 | 6,15-dihydroanthrazine-5,9,14,18-tetrone |
| CI 77491 | Diiron trioxide |
| CI 77492 | Iron oxide |
| CI 77499 | Triiron tetraoxide |
| CI 77891 | Titanium dioxide |
| CI 77947 | Zinc oxide |
| CINNAMIDOPROPYL TRIMONIUM CHLORIDE | |
| CINNAMOMUM CAMPHORA | |
| CITRIC ACID | Citric acid |
| *CITRUS AURANTIFOLIA* | *Citrus limetta*, ext. Extractives and their physically modified derivatives such as tinctures, concretes, absolutes, essential oils, oleoresins, terpenes, terpene-free fractions, distillates, residues, etc., obtained from *Citrus limetta*, Rutaceae |
| *CITRUS AURANTIUM* DULCIS CITRUS DULCIS | Orange, sweet, ext. Extractives and their physically modified derivatives such as tinctures, concretes, absolutes, essential oils, oleoresins, terpenes, terpene-free fractions, distillates, residues, etc., obtained from *Citrus sinensis*, Rutaceae |
| *CITRUS GRANDIS* | Grapefruit, ext. Extractives and their physically modified derivatives such as tinctures, concretes, absolutes, essential oils, oleoresins, terpenes, terpene-free fractions, distillates, residues, etc., obtained from *Citrus paradisi* M., Rutaceae |
| *CITRUS LIMONUM* | Lemon, ext. Extractives and their physically modified derivatives such as tinctures, concretes, absolutes, essential oils, oleoresins, terpenes, terpene-free fractions, distillates, residues, etc., obtained from *Citrus limonum*, Rutaceae |
| COCAMIDE DEA | Amides, coco, N,N-bis(hydroxyethyl) |
| COCAMIDOPROPYL BETAINE | 1-Propanaminium, 3-amino-N-(carboxy-methyl)-N,N-dimethyl-, N-coco acyl derivs., hydroxides, inner salts |
| COCAMIDOPROPYL HYDROXYSULTAINE | 1-Propanaminium, N-(3-aminopropyl)-2-hydroxy-N,N-dimethyl-3-sulfo-, N-coco acyl derivs., hydroxides, inner salts |
| COCAMIDOPROPYL PG-DIMONIUM CHLORIDE PHOSPHATE | Phosphoric acid, triester with N-(2,3-dihydroxypropyl)-N,N-dimethyl-3-[(1-oxococoalkyl)amino-1-propanaminium chloride |
| COCO-BETAINE | Betaines, coco alkyldimethyl |
| COCO-CAPRYLATE/CAPRATE | Alcohols, coco, mixed esters with octanoic and decanoic acids |
| COCODIMONIUM HYDROXYPROPYL HYDROLYZED WHEAT PROTEIN | |
| COCODIMONIUM HYDROXYPROPYL SILK AMINO ACIDS | |
| *COCOS NUCIFERA* | Coconut oil. Extractives and their physically modified derivatives. It consists primarily of the glycerides of the fatty acids capric, lauric, myristic, oleic and palmitic. (*Cocos nucifera*, Palmae); Extractives and their physically modified derivatives su |

TABLE 1-continued

| CONSTITUENT (INCI Name) | Other Chemical Name |
|---|---|
| COLLAGEN | Collagens. A fibrous protein comprising one third of the total protein in mammalian organisms. It is a polypeptide containing three peptide chains and rich in proline and hydroxyproline |
| COLLOIDAL SULFUR | Sulfur and gum arabic |
| COMMIPHORA MYRRHA84929-26- | Commiphora myrrha, ext. Extractives and their physically modified derivatives such as tinctures, concretes, absolutes, essential oils, oleoresins, terpenes, terpene-free fractions, distillates, residues, etc., obtained from *Commiphora myrrha*, Burseraceae |
| *COPERNICIA CERIFERA* | |
| *CORIANDRUM SATIVUM* | Coriander, ext. Extractives and their physically modified derivatives such as tinctures, concretes, absolutes, essential oils, oleoresins, terpenes, terpene-free fractions, distillates, residues, etc., obtained from *Coriandrum sativum*, Umbelliferae |
| CORN FLOWER EXTRACTS | |
| *CUCUMIS SATIVUS* | Cucumber, ext. Extractives and their physically modified derivatives such as tinctures, concretes, absolutes, essential oils, oleoresins, terpenes, terpene-free fractions, distillates, residues, etc., obtained from *Cucumis sativus*, Cucurbitaceae |
| *CUPRESSUS SEMPERVIRENS* | Cypress, Cupressus sempervirens, ext. Extractives and their physically modified derivatives such as tinctures, concretes, absolutes, essential oils, oleoresins, terpenes, terpene-free fractions, distillates, residues, etc., obtained from *Cupressus semper* |
| CYCLOHEXYLAMINE | |
| CYCLOMETHICONE | Octamethylcyclotetrasiloxane/decamethyl-cyclopentasiloxane |
| CYCLOMETHICONE DIMETHICONOL | |
| CYCLOPENTASILOXANE | |
| *CYMBOPOGON CITRATUS* | |
| *DAUCUS CAROTA* | Carrot, ext. Extractives and their physically modified derivatives such as tinctures, concretes, absolutes, essential oils, oleoresins, terpenes, terpene-free fractions, distillates, residues, etc., obtained from *Daucus carota*, Umbelliferae |
| DEA-OLETH-10 PHOSPHATE | Ethanol, 2,2'-iminobis-, compd. with (Z)-, a-9-octadecenyl-, ?-hydroxypoly(oxy-1,2-ethanediyl), phosphate |
| DEA-OLETH-3 PHOSPHATE | Ethanol, 2,2'-iminobis-, compd. with (Z)-, a-9-octadecenyl-, ?-hydroxypoly(oxy-1,2-ethanediyl), phosphate |
| DECYL GLUCOSIDE | Decyl D-glucoside |
| DENATONIUM BENZOATE | Denatonium benzoate |
| DIAZOLIDINYL UREA | 1-[1,3-bis(hydroxymethyl)-2,5-dioxoimida-zolidin-4-yl]-1,3-bis(hydroxymethyl)urea |
| DIISOBUTYL ADIPATE | Diisobutyl adipate |
| DIISOPROPYL ADIPATE | Diisopropyl adipate |
| DIISOPROPYL DIMER DILINOLEATE | |
| DIISOSTEAROYL TRIMETHYLOLPROPANE SILOXY SILICATE | |
| DIMETHICONAL | |
| DIMETHICONE | Dimethicone |
| DIMETHICONE BISAMINO HYDROXYPROPYL COPOLYOL/ ALGAE/ALOE BARBADENSIS/ CHAMOMILE/HENNA/JOJOBA/ ROSEMARY/DIMETHICONE COPOLYOL | |
| DIMETHICONE BISAMINO HYDROXYPROPYL COPOLYOL/ GLUTAMINE/TYROSINE/LEUCINE/ CYSTEINE/GLYSINE/COMFREY/ PLANTAIN/HYDROLYZED WHEAT PROTEIN/ DIMETHICONE COPOLYOL | |
| DIMETHICONE BISAMINO HYDROXYPROPYL COPOLYOL/ WHITE GINGER/ DIMETHICONE COPOLYOL | |
| DIMETHICONE COPOLYOL | Siloxanes and silicones, di-me, hydroxy-terminated, ethoxylated propoxylated |

TABLE 1-continued

| CONSTITUENT (INCI Name) | Other Chemical Name |
|---|---|
| DIMETHICONE COPOLYOL ACETATE | |
| DIMETHICONE PROPYL PG-BETAINE | |
| DIMETHICONOL | Poly[oxy(dimethylsilylane)], a-hydro-?-hydroxy- |
| DIMETHYL ETHER | Dimethyl ether |
| DIMETHYL LAURAMINE ISOSTEARATE | Isooctadecanoic acid, compound with N,N-dimethyldodecylamine (1:1) |
| DIPENTAERYTHRITYL HEXACAPRYLATE/HEXACAPRATE | Decanoic acid, ester with 2,2'-[oxybis(methylene)]bis[2-(hydroxymethyl)-1,3-propanediol] octanoate pentanoate |
| DIPHENYL DIMETHICONE | |
| DIPOTASSIUM GLY-CYRRHIZATE | a-d-Glucopyranosiduronic acid, (3á,20á)-20-carboxy-11-oxo-30-norolean-12-en-3-yl 2-O-á-d-glucopyranuronosyl-, dipotassium salt |
| DIPROPYLENE GLYCOL | 1,1'-oxydipropan-2-ol |
| DISODIUM COCO-AMPHODIPROPIONATE | Imidazolium compounds, 1-[2-(2-carboxy-ethoxy)ethyl]-1(or 3)-(2-carboxyethyl)-4,5-dihydro-2-norcoco alkyl, hydroxides, disodium salts |
| DISODIUM EDTA | Disodium dihydrogen ethylenediaminetetraacetate |
| DISTEAROYLETHYL HYDROXYETHYLMONIUM METHOSULFATE | |
| DISTEARYLDIMONIUM CHLORIDE | Dimethyldioctadecylammonium chloride |
| DMDM HYDANTOIN | 1,3-bis(hydroxymethyl)-5,5-dimethylimida-zolidine-2,4-dione |
| EDTA | Edetic acid |
| EMULSIFYING WAX NF | |
| *EQUISETUM ARVENSE* | *Equisetum arvense*, ext. Extractives and their physically modified derivatives such as tinctures, concretes, absolutes, essential oils, oleoresins, terpenes, terpene-free fractions, distillates, residues, etc., obtained from *Equisetum arvense*, Equisetacea |
| ESTER CAPRYLIC | |
| ETHOXYDIGLYCOL | 2-(2-ethoxyethoxy)ethanol |
| ETHYL ESTER OF HYDROLYZED SILK | |
| ETHYL ESTER OF PVM/MA COPOLYMER | 2-butanedioic acid (Z)-, monoethyl ester, polymer with methoxyethene |
| ETHYLHEXYL METHOXY-CINNAMATE | |
| ETHYLHEXYL STEARATE | |
| ETHYLPARABEN | Ethyl 4-hydroxybenzoate |
| *EUCALYPTUS GLOBULUS* | *Eucalyptus globulus*, ext. Extractives and their physically modified derivatives such as tinctures, concretes, absolutes, essential oils, oleoresins, terpenes, terpene-free fractions, distillates, residues, etc., obtained from *Eucalyptus globulus*, Myrtace |
| FACTOR 12 | |
| FLAVOUR | |
| GLUCOSAMINE HCl | Glucosamine hydrochloride |
| GLUTAMIC ACID | Glutamic acid; DL-glutamic acid monohydrate |
| GLYCERIN | Glycerol |
| GLYCERYL STEARATE | Stearic acid, monoester with glycerol |
| GLYCINE | Glycine |
| *GLYCINE SOJA* | Soybean oil. Extractives and their physically modified derivatives. It consists primarily of the glycerides of the fatty acids linoleic, oleic, palmitic and stearic. (*Soja hispida*, Leguminosae) |
| GLYCYRRHIZIC ACID | Glycyrrhizic acid |
| GLYOXYLIC ACID | Glyoxylic acid |
| GUAR HYDROXYPROPYL-TRIMONIUM CHLORIDE | Guar gum, 2-hydroxy-3-(trimethylammonio)propyl ether, chloride |
| *HAMAMELIS VIRGINIANA* | *Hamamelis virginiana*, ext. Extractives and their physically modified derivatives such as tinctures, concretes, absolutes, essential oils, oleoresins, terpenes, terpene-free fractions, distillates, residues, etc., obtained from *Hamamelis virginiana*, Hamam |
| HC RED NO. 3 | 2-(4-amino-2-nitroanilino)ethanol |
| HC YELLOW NO. 5 | 2-(2-amino-4-nitroanilino)ethanol |
| *HELIANTHUS ANNUUS* | Extractives and their physically modified derivatives such as tinctures, concretes, absolutes, essential oils, |

TABLE 1-continued

| CONSTITUENT (INCI Name) | Other Chemical Name |
|---|---|
| | oleoresins, terpenes, terpene-free fractions, distillates, residues, etc., obtained from *Helianthus annuus*; Oils, sunflower, unsaponifiables fr |
| HEXAMIDINE PARABEN | P-hydroxybenzoic acid, compound with p,p'-[hexane-1,6-diylbis(oxy)]bis(benzamidine) (2:1) |
| HEXYLENE GLYCOL | 2-methylpentane-2,4-diol |
| HOPS EXTRACT | |
| HYALURONIC ACID | Hyaluronic acid |
| *HYDRASTIS CANADENSIS* | Golden seal, *Hydrastis canadensis*, ext. Extractives and their physically modified derivatives such as tinctures, concretes, absolutes, essential oils, oleoresins, terpenes, terpene-free fractions, distillates, residues, etc., obtained from *Hydrastis cana* |
| HYDROABIETYL ALCOHOL | [1R-(1a,4aá,4ba,10aa)]-dodecahydro-7-isopropyl-1,4a-dimethylphenanthren-1-methanol |
| HYDROFLUOROCARBON 152A | 1,1-difluoroethane |
| HYDROGEN PEROXIDE | Hydrogen peroxide |
| HYDROGENATED BUTYLENE/ ETHYLENE/STYRENE COPOLYMER | |
| HYDROGENATED CASTOR OIL | Castor oil, hydrogenated |
| HYDROGENATED COCONUT OIL | Coconut oil, hydrogenated |
| HYDROGENATED ETHYLENE/ PROPYLENE/STYRENE COPOLYMER | |
| HYDROGENATED MICROCRYSTALLINE WAX | Paraffin waxes and Hydrocarbon waxes, microcryst., hydrotreated. A complex combination of hydrocarbons obtained from residual oils by solvent crystallisation and treated with hydrogen in the presence of a catalyst. It consists predominantly of saturated s |
| HYDROGENATED ROSIN | |
| HYDROGENATED TAL-LOWETH-60 MYRISTYL GLYCOL | |
| HYDROLYZED COLLAGEN | Collagens, hydrolyzates. Substance obtained by acidic, alkaline, or enzymatic hydrolysis of hoofs and horns composed primarily of amino acids, peptides, and proteins. It may contain impurities consisting chiefly of carbohydrates and lipids along with small |
| HYDROLYZED KERATIN | Keratins, hydrolyzates. A biological material consisting predominantly of partially hydrolyzed keratin |
| HYDROLYZED MUCO-POLYSACCHARIDES | |
| HYDROLYZED PROTEIN | |
| HYDROLYZED SILK | Protein hydrolyzates, silk |
| HYDROLYZED SOY PROTEIN | Protein hydrolyzates, soya. Substance obtained by acidic, alkaline, or enzymatic hydrolysis of soya composed primarily of amino acids, peptides, and proteins. It may contain impurities consisting chiefly of carbohydrates and lipids along with smaller quan |
| HYDROLYZED VEGETABLE PROTEIN | Protein hydrolyzates, vegetable. Substance obtained by acidic, alkaline, or enzymatic hydrolysis of mixed vegetables composed primarily of amino acids, peptides, and proteins. It may contain impurities consisting chiefly of carbohydrates and lipids along |
| HYDROLYZED WHEAT GLUTEN | |
| HYDROLYZED WHEAT PROTEIN | Protein hydrolyzates, wheat germ. Substance obtained by acidic, alkaline, or enzymatic hydrolysis of wheat germ composed primarily of amino acids, peptides, and proteins. It may contain impurities consisting chiefly of carbohydrates and lipids along with |
| HYDROLYZED WHEAT PROTEIN/PVP CROSS-POLYMER | |
| HYDROLYZED WHEAT STARCH | |
| HYDROXYETHYL CETYLDIMONIUM PHOSPHATE | Hexadecyl(2-hydroxyethyl)dimethylammonium dihydrogen phosphate |
| HYDROXYETHYLCELLULOSE | Cellulose, 2-hydroxyethyl ether |
| HYDROXYLATED LANOLIN | Lanolin, hydroxylated |
| HYDROXYPROPYL BISSTEARYLDIMONIUM CHLORIDE | 1,3-propanediaminium, 2-hydroxy-N,N'-bis(octadecyl)-N,N,N',N'-tetramethyl-, chloride |
| HYDROXYPROPYL GUAR | Guar gum, 2-hydroxypropyl ether, |
| HYDROXYPROPYL GUAR HYDROXYPROPYLTRIMONIUM CHLORIDE | |

TABLE 1-continued

| CONSTITUENT (INCI Name) | Other Chemical Name |
|---|---|
| HYDROXYPROPYL METHYLCELLULOSE | Cellulose, 2-hydroxypropyl methyl ether |
| HYDROXYPROPYLCELLULOSE | Cellulose, 2-hydroxypropyl ether |
| HYDROXYPROPYLTRIMONIUM HYDROLYZED WHEAT PROTEIN | |
| HYDROXYSTEARIC ACID | 12-hydroxystearic acid |
| HYPERICUM PERFORA-TUM | St.-John's-wort, *Hypericum perforatum*, ext. Extractives and their physically modified derivatives such as tinctures, concretes, absolutes, essential oils, oleoresins, terpenes, terpene-free fractions, distillates, residues, etc., obtained from Hypericu |
| I.P.M. | |
| IMIDAZOLIDINYL UREA | N,N''-methylenebis[N'-[3-(hydroxymethyl)-2,5-dioxoimidazolidin-4-yl]urea] |
| INOSITOL | Myo-inositol |
| IODOPROPYNYL BUTYL-CARBAMATE | 3-iodo-2-propynyl butylcarbamate |
| IRON OXIDE | Diiron trioxide (CI 77489, 77491, 77492, 77499); Magnesium oxide (CI 77489, 77491, 77492, 77499); Triiron tetraoxide (CI 77489, 77491, 77492, 77499) |
| ISOBUTANE | Isobutane |
| ISOBUTYLPARABEN | Isobutyl 4-hydroxybenzoate |
| ISOCETETH-20 | |
| ISODODECANE | Isododecane |
| ISOHEXADECANE | 2,2,4,4,6,8,8-heptamethylnonane |
| ISOLAURETH-6 | |
| ISOPENTANE | 2-methylbutane |
| ISOPROPYL ALCOHOL | Propan-2-ol |
| ISOPROPYL C12-15-PARETH-9 CARBOXYLATE | |
| ISOPROPYL LANOLATE | Fatty acids, lanolin, iso-Pr esters |
| ISOPROPYL MYRISTATE | Isopropyl myristate |
| ISOPROPYL STEARATE | Isopropyl stearate |
| ISOPROPYLPARABEN | Isopropyl 4-hydroxybenzoate |
| ISOSTEARETH-10 | Poly(oxy-1,2-ethanediyl), a-isooctadecyl-?-hydroxy- |
| ISOSTEARETH-20 | Poly(oxy-1,2-ethanediyl), a-isooctadecyl-?-hydroxy- |
| ISOSTEARYL PALMITATE | Isooctadecyl palmitate |
| *JUNIPERUS COMMUNIS* | Juniper, *Juniperus communis*, ext. Extractives and their physically modified derivatives such as tinctures, concretes, absolutes, essential oils, oleoresins, terpenes, terpene-free fractions, distillates, residues, etc., obtained from *Juniperus communis*, |
| KAOLIN | Naturally occurring substances, kaolin (CI 77004) |
| KAWA EXTRACT | |
| KERATIN | Keratins. Natural, fibrous proteins occurring in vertebrates. They contain all of the common amino acids and are characterized by high cystine content |
| KERATIN AMINO ACIDS | Keratins, hydrolyzates |
| LACTAMIDE MEA | N-2-hydroxyethyllactamide |
| LACTIC ACID | Lactic acid |
| LAMINARIA DIGITATE | |
| LANETH-10 | Alcohols, lanolin, ethoxylated |
| LANOLIN | Lanolin. Fat-like substance derived from sheep wool. Contains a complex combination of esters and polyesters, consisting chiefly of cholesteryl and isocholesteryl esters of the higher fatty acids |
| LANOLIN ALCOHOL | Alcohols, lanolin. A complex combination of organic alcohols obtained by the hydrolysis of lanolin |
| LANOLIN CERA | Lanolin, wax. Wax obtained by fractionation of anhydrous lanolin |
| LAURETH-23 | Poly(oxy-1,2-ethanediyl), a-dodecyl-?-hydroxy- |
| LAURETH-4 | 3,6,9,12-tetraoxatetracosan-1-ol |
| LAURETH-7 | 3,6,9,12,15,18,21-heptaoxatritriacontanol |
| LAURYL ALCOHOL | Dodecan-1-ol |
| LAURYL METHYL GLU-CETH-10 HYDROXYPROPYLDIMONIUM CHLORIDE | |
| LAURYLDIMONIUM HYDROXYPROPYL HYDROLYZED COLLAGEN | Lamanequat L |
| LAVANDULA ANGUSTI-FOLIA | Lavender, *Lavandula angustifolia*, ext. Extractives and their physically modified derivatives such as tinctures, concretes, absolutes, essential oils, oleoresins, terpenes, terpene-free fractions, distillates, residues, etc., obtained from *Lavandula angus* |
| *LAWSONIA INERMIS* | *Lawsonia inermis*, ext. Extractives and their physically modified derivatives such as tinctures, concretes, |

TABLE 1-continued

| CONSTITUENT (INCI Name) | Other Chemical Name |
|---|---|
| | absolutes, essential oils, oleoresins, terpenes, terpene-free fractions, distillates, residues, etc., obtained from *Lawsonia inermis*, Lythraceae |
| LECITHIN | Lecithins. The complex combination of diglycerides of fatty acids linked to the choline ester of phosphoric acid |
| LEMONGRASS EXTRACT | |
| LINOLEAMIDOPROPYL ETHYLDIMONIUM ETHOSULFATE | 1-propanaminium, N-ethyl-N,N-dimethyl-3-antistatic [1-oxo-9,12-octadecadienylamino]-, ethyl sulfate (salt) |
| LINOLEAMIDOPROPYL PG-DIMONIUM CHLORIDE PHOSPHATE | 1-propanaminium, 2,3-dihydroxy-N,N-dimethyl-N-[3-(1-oxo-9,12-octadecadienyl-amino)propyl]-, 3-phosphate triester, trichloride |
| LINOLEIC ACID | Linoleic acid |
| LINOLENIC ACID | Linolenic acid |
| LUVISKOL | |
| LYSINE | L-lysine |
| MAGNESIUM ALUMINUM SILICATE | Silicic acid, aluminum magnesium salt |
| MAGNESIUM CHLORIDE7786-30-3 | Magnesium chloride |
| MAGNESIUM NITRATE | Magnesium nitrate |
| *MALVA SYLVESTRIS* | Mallow, *Malva sylvestris*, ext. Extractives and their physically modified derivatives such as tinctures, concretes, absolutes, essential oils, oleoresins, terpenes, terpene-free fractions, distillates, residues, etc., obtained from *Malva sylvestris*, Malva |
| MEADOWFOAM SEED OIL | |
| *MELISSA OFFICINALIS* | *Melissa officinalis*, ext. Extractives and their physically modified derivatives such as tinctures, concretes, absolutes, essential oils, oleoresins, terpenes, terpene-free fractions, distillates, residues, etc., obtained from *Melissa officinalis*, Labiata |
| METHACRYLOYL ETHYL BETAINE/ ACRYLATES COPOLYMER | Amersette |
| METHYL GLUCETH-10 | Poly(oxy-1,2-ethanediyl), a-hydro-?-hydroxy-, ether with methyl á-d-glucopyranoside (4:1) |
| METHYL GLUCETH-20 | Poly(oxy-1,2-ethanediyl), a-hydro-?-hydroxy-, ether with methyl á-d-glucopyranoside (4:1) |
| METHYL HYDROGENATED ROSINATE | Resin acids and Rosin acids, hydrogenated, Me esters |
| METHYLAL | Dimethoxymethane |
| METHYLCHLOROISOTHI26172-55-4 AZOLINONE | 5-chloro-2-methyl-2H-isothiazol-3-one |
| METHYLDIBROMO GLU-TARONITRILE | 2-bromo-2-(bromomethyl)pentanedinitrile |
| METHYLDIHYDRO-JASMONATE | Methyl (1R-trans)-3-oxo-2-pentylcyclopentaneacetate |
| METHYLISOTHIAZOLIN ONE | 2-methyl-2H-isothiazol-3-one |
| METHYLPARABEN | Methyl 4-hydroxybenzoate |
| MICA | Mica-group minerals (CI 77019) |
| MICROWAX 80 | |
| MINERAL OIL | |
| MUSK KETONE | |
| MYRISTAMINE OXIDE | N,N-dimethyltetradecylamine N-oxide |
| MYRISTOYL HYDROLYZED COLLAGEN | Gelatins, hydrolyzates, myristoyl derivativesantistatic |
| NETTLE EXTRACT | |
| NIACINAMIDE | Nicotinamide |
| NIPASEPT SODIUM | |
| NITROMETHANE | Nitromethane |
| NONOXYNOL-10 | 29-(nonylphenoxy)-3,6,9,12,15,18,21,24,27-nonaoxanonacosanol |
| NONOXYNOL-14 | Poly(oxy-1,2-ethanediyl), a-(nonylphenyl)-?-hydroxy- |
| *OCIMUM BASILICUM* | *Ocimum basilicum*, ext. Extractives and their physically modified derivatives such as tinctures, concretes, absolutes, essential oils, oleoresins, terpenes, terpene-free fractions, distillates, residues, etc., obtained from *Ocimum basilicum*, Labiatae |
| OCTOXYNOL-40 | Poly(oxy-1,2-ethanediyl), a-[4-(1,1,3,3-tetramethylbutyl)phenyl]-?-hydroxy- |
| OCTYL METHOXYCINNAMATE | 2-ethylhexyl 4-methoxycinnamate |
| OCTYL PALMITATE | 2-ethylhexyl palmitate |
| OCTYL SALICYLATE | 2-ethylhexyl salicylate |
| OCTYL STEARATE | 2-ethylhexyl stearate |
| OCTYLACRYLAMIDE/ACRYLATES/ BUTYLAMI-NOETHYL METHACRYLATE COPOLYMER | |

TABLE 1-continued

| CONSTITUENT (INCI Name) | Other Chemical Name |
|---|---|
| OCTYLDODECANOL | 2-octyldodecan-1-ol |
| OCTYLDODECYL NEOPENTANOATE | Propanoic acid, 2,2-dimethyl-, 2-octyldodecyl ester |
| *OENOTHERA BIENNIS* | Evening primrose, *Oenothera biennis*, ext. Extractives and their physically modified derivatives such as tinctures, concretes, absolutes, essential oils, oleoresins, terpenes, terpene-free fractions, distillates, residues, etc., obtained from Oenothera bi |
| *OLEA EUROPAEA* | Olive oil. Extractives and their physically modified derivatives. It consists primarily of the glycerides of the fatty acids linoleic, oleic and palmitic. (*Olea europaea*, Oleaceae) |
| OLEAMIDOPROPYL PG-DIMONIUM CHLORIDE | 1-propanaminium, 3-[(1-oxo-9-octa-decenyl)amino]-N-(2, 3-dihydroxypropyl)-N,N-dimethyl-, chloride |
| OLETH-10 | Poly(oxy-1,2-ethanediyl), a-9-octadecenyl-?-hydroxy- |
| OLETH-2 | Poly(oxy-1,2-ethanediyl), a-9-octadecenyl-?-hydroxy- |
| OLETH-20 | Poly(oxy-1,2-ethanediyl), a-9-octadecenyl-?-hydroxy- |
| OLETH-3 | Poly(oxy-1,2-ethanediyl), a-9-octadecenyl-?-hydroxy- |
| OLETH-3 PHOSPHATE | Poly(oxy-1,2-ethanediyl), a-9-octadecenyl-?-hydroxy-(Z)-, phosphate |
| OLETH-5 | Poly(oxy-1,2-ethanediyl), a-9-octadecenyl-?-hydroxy- |
| OLEYL ALCOHOL | (Z)-octadec-9-enol |
| ORANGE PEEL WAX | Waxes, orange peel |
| *ORYZA SATIVA* | Starch. High-polymeric carbohydrate material usually derived from cereal grains such as corn, wheat and *sorghum*, and from roots and tubers such as potatoes and tapioca. Includes starch which has been pregelatinized by heating in the presence of water |
| ORYZANOL | (?)-oryzanol |
| OZOKERITE | Hydrocarbon waxes (petroleum), chemically neutralized. A complex combination of hydrocarbons produced by a treating process to remove acidic materials. It consists predominantly of saturated straight chain hydrocarbons having carbon numbers predominantly |
| PABA | 4-aminobenzoic acid |
| PANAX GINSENG | Ginseng, *Panax pseudoginseng*, ext. Extractives and their physically modified derivatives such as tinctures, concretes, absolutes, essential oils, oleoresins, terpenes, terpene-free fractions, distillates, residues, etc., obtained from *Panax pseudoginseng* |
| PANTHENOL | Dexpanthenol |
| PANTHENYL ETHYL ETHER | (+)-N-(3-ethoxypropyl)-2,4-dihydroxy-3,3-dimethylbutyramide |
| PANTHENYL HYDROXY-PROPYL STEARDIMONIUM CHLORIDE | 1-octadecanaminium, N,N-dimethyl-N-[2-hydroxy-3-[2, 2-dimethyl-3-hydroxy-4-oxo-4-(3-hydroxypropyl)amino]butyl]-, chloride |
| PARAFFIN | Paraffin waxes and Hydrocarbon waxes. A complex combination of hydrocarbons obtained from petroleum fractions by solvent crystallization (solvent deoiling) or by the sweating process. It consists predominantly of straight chain hydrocarbons having carbon |
| PARAFFINUM LIQUIDUM | Paraffin oils. Liquid hydrocarbons from petroleum |
| PERFUME | |
| PCA | Pidolic acid |
| PEG/PPG 25/25 DIMETHICONE/ACRYLATES COPOLYMER | |
| PEG/PPG-14/4 DIMETHICONE | |
| PEG-10 SOYA STEROL | |
| PEG-100 STEARATE | Poly(oxy-1,2-ethanediyl), a-(1-oxooctadecyl)-?-hydroxy- |
| PEG-12 | 3,6,9,12,15,18,21,24,27,30,33-undecaoxapentatriacontane-1,35-diol |
| PEG-15 COCOPOLYAMINE | |
| PEG-150/STEARYL ALCOHOL/SMDI COPOLYMER | |
| PEG-150 DISTEARATE | Poly(oxy-1,2-ethanediyl), a-(1-oxooctadecyl)-?-[(1-oxooctadecyl)oxy]- |
| PEG-150 PENTAERYTHRITYL TETRASTEARATE | |
| PEG-192 APRICOT KERNEL GLYCERIDES | |
| PEG-2 DIMEADOWFOAM AMIDOETHYLMONIUM METHOSULFATE | |

TABLE 1-continued

| CONSTITUENT (INCI Name) | Other Chemical Name |
|---|---|
| PEG-2 OLEAMMONIUM CHLORIDE | Bis(hydroxyethyl)methyloleylammonium chloride |
| PEG-20 STEARATE | Poly(oxy-1,2-ethanediyl), a-(1-oxooctadecyl)-?-hydroxy- |
| PEG-25 HYDROGENATED CASTOR OIL | Castor oil, hydrogenated, ethoxylated |
| PEG-25 PABA | |
| PEG-32 | Poly(oxy-1,2-ethanediyl), a-hydro-?-hydroxy-humectants |
| PEG-4 | 3,6,9-trioxaundecane-1,11-diol |
| PEG-40 | Poly(oxy-1,2-ethanediyl), a-hydro-?-hydroxy-humectants |
| PEG-40 CASTOR OIL | Castor oil, ethoxylated |
| PEG-40 HYDROGENATED CASTOR OIL | Castor oil, hydrogenated, ethoxylated |
| PEG-40 SORBITAN LANOLATE | G 1441 |
| PEG-45 PALM KERNEL GLYCERIDES | |
| PEG-45M | Poly(oxy-1,2-ethanediyl), a-hydro-?-hydroxy- |
| PEG-5 OCTANOATE | |
| PEG-5M | Poly(oxy-1,2-ethanediyl), a-hydro-?-hydroxy- |
| PEG-6 CAPRYLIC/CAPRIC GLYCERIDES | |
| PEG-6 COCAMIDE | Fatty acids, coco, reaction products with ethanolamine, ethoxylated |
| PEG-60 | Poly(oxy-1,2-ethanediyl), a-hydro-?-hydroxy- |
| PEG-60 ALMOND GLYCERIDES | |
| PEG-60 HYDROGENATED CASTOR OIL | Castor oil, hydrogenated, ethoxylated |
| PEG-7 GLYCERYL COCOATE | Glycerides, coco mono-and di-, ethoxylated |
| PEG-70 MANGO GLYCERIDES | |
| PEG-75 | Poly(oxy-1,2-ethanediyl), a-hydro-?-hydroxy- |
| PEG-75 LANOLIN | Lanolin, ethoxylated |
| PEG-75 SHEA BUTTER GLYCERIDES | |
| PEG-8 | 3,6,9,12,15,18,21-heptaoxatricosane-1,23-diol |
| PEG-8 BEESWAX | |
| PEG-9 COCOGLYCERIDES | |
| PEG-90M | Poly(oxy-1,2-ethanediyl), a-hydro-?-hydroxy- |
| PELVETIA DIGITATA | |
| PENTAERYTHRITYL TETRACAPRYLATE/CAPRATE | Decanoic acid, mixed esters with octanoic acid and pentaerythritol |
| PENTANE | Pentane |
| PENTASODIUM PENTE-TATE | Pentasodium (carboxylatomethyl)iminobis(ethylenenitrilo)tetraacetate |
| PERSEA GRATISSIMA | Oils, avocado. Extractives and their physically modified derivatives. It consists primarily of the glycerides of the fatty acids linoleic, oleic, and palmitic. (*Persea americana*, Lauraceae) |
| PETROLATUM | Petrolatum. A complex combination of hydrocarbons obtained as a semi-solid from dewaxing paraffinic residual oil. It consists predominantly of saturated crystalline and liquid hydrocarbons having carbon numbers predominantly greater than C25 |
| PHENOXYETHANOL | 2-phenoxyethanol |
| PHENYL TRIMETHICONE | 1,1,5,5,5-hexamethyl-3-phenyl-3-[(trimethylsilyl)oxy]trisiloxane |
| PHOSPHATE | |
| PHYTANTRIOL | 3,7,11,15-tetramethylhexadecane-1,2,3-triol |
| *POGOSTEMON CABLIN* | *Patchouli*, ext. Extractives and their physically modified derivatives such as tinctures, concretes, absolutes, essential oils, oleoresins, terpenes, terpene-free fractions, distillates, residues, etc., obtained from Pogostemon cablin (*Pogostemon patchoul* |
| POLYACRYLAMIDE | 2-propenamide, homopolymer |
| POLYACRYLAMIDO-METHYLPROPANE SULFONIC ACID | |
| POLYBUTENE | polybutene-1, poly(1-butene), PB-1. |
| POLYISOBUTENE | 1-propene, 2-methyl-, homopolymer |
| POLYLENE GLYCOL | |
| POLYOXYL 40 | |
| POLYQUATERNIUM | |
| POLYQUATERNIUM-10 | Cellulose, 2-(2-hydroxy-3-(trimethylammonium)propoxy)ethyl ether, chloride |
| POLYQUATERNIUM-11 | 2-propenoic acid, 2-methyl-, 2-(dimethyl-amino)ethyl ester, polymer with 1-ethenyl-2-pyrrolidinone, compd. with diethyl sulfate |
| POLYQUATERNIUM-16 | |
| POLYQUATERNIUM-37 | |
| POLYQUATERNIUM-4 | |
| POLYQUATERNIUM-46 | |

TABLE 1-continued

| CONSTITUENT (INCI Name) | Other Chemical Name |
|---|---|
| POLYQUATERNIUM-7 | 2-propen-1-aminium, N,N-dimethyl-N-2-propenyl-, chloride, polymer with 2-propenamide |
| POLYSILICONE-11 | |
| POLYSILICONE-8 | |
| POLYSILOXAN | |
| POLYSORBATE 20 | Sorbitan, monododecanoate, poly(oxy-1,2-ethanediyl) derivs |
| POLYSORBATE 40 | Sorbitan, monohexadecanoate, poly(oxy-1,2-ethanediyl) derivs |
| POLYSORBATE 60 | Sorbitan, monooctadecanoate, poly(oxy-1,2-ethanediyl) derivs |
| POLYSORBATE 80 | Sorbitan, mono-9-octadecenoate, poly(oxy-1,2-ethanediyl) derivs., (Z)- |
| POLYSTYRENE | Benzene, ethenyl-, homopolymer |
| POLYVINYL ALCOHOL | Ethenol, homopolymer |
| POLYVINYL CAPRO-LACTAM | |
| POTASSIUM HYDROXIDE | Potassium hydroxide |
| POTASSIUM SORBATE | Potassium (E,E)-hexa-2,4-dienoate |
| POTATO FLAKES | |
| POTATO STARCH MODIFIED | |
| PPG-1 TRIDECETH-6 | |
| PPG-10 METHYL GLUCOSE ETHER | Poly[oxy(methyl-1,2-ethanediyl)], a-hydro-?-hydroxy-, ether with methyl á-d-glucopyranoside (4:1) |
| PPG-12-PEG-50 LANOLIN | Lanolin, ethoxylated, propoxylated |
| PPG-20 METHYL GLUCOSE ETHER | Poly[oxy(methyl-1,2-ethanediyl)], a-hydro-?-hydroxy-, ether with methyl á-d-glucopyranoside (4:1) |
| PPG-3 METHYL ETHER | 1-[2-(2-methoxy-1-methylethoxy)-1-methylethoxy]propan-2-ol |
| PPG-3 MYRISTYL ETHER | Poly[oxy(methyl-1,2-ethanediyl)], a-tetradecyl-?-hydroxy- |
| PPG-5-CETETH-20 | Oxirane, methyl-, polymer with oxirane, hexadecyl ether |
| PROLINE | L-proline |
| PROPANE | Propane |
| PROPYLENE GLYCOL | Propane-1,2-diol |
| PROPYLENE GLYCOL DICAPRYLATE/DICAPRATE | Decanoic acid, mixed diesters with octanoic acid and propylene glycol |
| PROPYLPARABEN | Propyl 4-hydroxybenzoate |
| *PRUNUS DULCIS* | Almond, sweet, ext. Extractives and their physically modified derivatives such as tinctures, concretes, absolutes, essential oils, oleoresins, terpenes, terpene-free fractions, distillates, residues, etc., obtained from *Prunus amygdalus* sativa, Rosaceae; |
| PVM/MA DECADIENE CROSSPOLYMER | |
| PVP | 2-pyrrolidinone, 1-ethenyl-, homopolymer |
| PVP/DIMETHYLAMINO-30581-59-0 ETHYLMETHACRYLATE COPOLYMER | |
| PVP/VA | |
| PVP/VA COPOLYMER | Acetic acid, ethenyl ester, polymer with 1-ethenyl-2-pyrrolidinone |
| PVP/VINYLCAPROLACTUM/DMAPA ACRYLATES COPOLYMER | |
| PVP COPOLYMER | |
| *PYRUS MALUS* | Apple, *Malus pumila*, ext. Extractives and their physically modified derivatives such as tinctures, concretes, absolutes, essential oils, oleoresins, terpenes, terpene-free fractions, distillates, residues, etc., obtained from *Malus pumila*, Rosaceae |
| QUATERNIUM-26 | 1-Propanaminium, 3-amino-N-(2-hydroxy-ethyl)-N,N-dimethyl-, N-mink-oil acyl derivs., chlorides |
| QUATERNIUM-27 | Imidazolium compounds, 4,5-dihydro-1-methyl-2-nortallow alkyl-1-(2-tallow amidoethyl), Me sulfates |
| QUATERNIUM-52 | Poly(oxy-1,2-ethanediyl), a,a',a''-[(octade-cylnitrilio)tri-2,1-ethanediyl)tris(?-hydroxy)-, phosphate (1:1) (salt) |
| QUATERNIUM-70 | Dimethyl[3-[(1-oxooctadecyl)amino]propyl][2-oxo-2-(tetradecyloxy)ethyl]ammonium chloride |
| QUATERNIUM-79 HYDROLYZED KERATIN | |
| QUATERNIUM-79 HYDROLYZED SILK | |
| QUATERNIUM-79 HYDROLYZED SOY PROTEIN | |
| QUATERNIUM-87 | |

TABLE 1-continued

| CONSTITUENT (INCI Name) | Other Chemical Name |
|---|---|
| QUILLAIA SAPONARIA | *Quillaja saponaria*, ext. Extractives and their physically modified derivatives such as tinctures, concretes, absolutes, essential oils, oleoresins, terpenes, terpene-free fractions, distillates, residues, etc., obtained from *Quillaja saponaria*, Rosaceae |
| RETINYL PALMITATE | Retinyl palmitate |
| RHUS SUCCEDANEA | Rhus succedanea, ext. Extractives and their physically modified derivatives such as tinctures, concretes, absolutes, essential oils, oleoresins, terpenes, terpene-free fractions, distillates, residues, etc., obtained from Rhus succedanea, Anacardiaceae |
| *RICINUS COMMUNIS* | Castor oil. Extractives and their physically modified derivatives. It consists primarily of the glycerides of the fatty acid ricinoleic. (*Ricinus communis*, Euphorbiaceae) |
| *ROSA CANINA* | Rose, *Rosa canina*, ext. Extractives and their physically modified derivatives such as tinctures, concretes, absolutes, essential oils, oleoresins, terpenes, terpene-free fractions, distillates, residues, etc., obtained from *Rosa canina*, Rosaceae |
| *ROSMARINUS OFFICINALIS* | Rosemary, ext. Extractives and their physically modified derivatives such as tinctures, concretes, absolutes, essential oils, oleoresins, terpenes, terpene-free fractions, distillates, residues, etc., obtained from *Rosmarinus officinalis*, Labiatae |
| *SACCHAROMYCES*/COPPER FERMENT | |
| *SACCHAROMYCES*/IRON FERMENT | |
| *SACCHAROMYCES*/MAGNESIUM FERMENT | |
| *SACCHAROMYCES*/SILICON FERMENT | |
| *SACCHAROMYCES*/ZINC FERMENT | |
| *SACCHARUM OFFICINARUM* | Sugarcane, ext. Extractives and their physically modified derivatives such as tinctures, concretes, absolutes, essential oils, oleoresins, terpenes, terpene-free fractions, distillates, residues, etc., obtained from *Saccharum officinarum*, Gramineae |
| *SALVIA OFFICINALIS* | Sage, *Salvia officinalis*, ext. Extractives and their physically modified derivatives such as tinctures, concretes, absolutes, essential oils, oleoresins, terpenes, terpene-free fractions, distillates, residues, etc., obtained from *Salvia officinalis*, Lab |
| *SANTALUM ALBUM* | Sandalwood, ext. Extractives and their physically modified derivatives such as tinctures, concretes, absolutes, essential oils, oleoresins, terpenes, terpene-free fractions, distillates, residues, etc., obtained from *Santalum album*, Santalaceae |
| SERENOA SERRULATA | *Sabal serrulatum*, ext. Extractives and their physically modified derivatives such as tinctures, concretes, absolutes, essential oils, oleoresins, terpenes, terpene-free fractions, distillates, residues, etc., obtained from *Sabal serrulatum*, Palmae |
| SERINE | L-serine |
| *SESAMUM INDICUM* | Oils, sesame. Extractives and their physically modified derivatives. It consists primarily of the glycerides of the fatty acids linoleic, oleic, palmitic and stearic. (*Sesamum indicum*, Pedaliaceae) |
| SHEA BUTTER | |
| SILICA | Silicon dioxide |
| SILK AMINO ACIDS | Protein hydrolyzates, silk |
| SIMENTHICON | |
| SIMETHICONE | |
| SODIUM ACRYLOYLDI-METHYLTAURATE COPOLYMER | |
| SODIUM BENZOATE | Sodium benzoate |
| SODIUM BISULFITE | Sodium hydrogensulphite |
| SODIUM CHLORIDE | Sodium chloride |
| SODIUM COCOYL HYDROLYZED SOY PROTEIN | |
| SODIUM HYDROXIDE | Sodium hydroxide |

TABLE 1-continued

| CONSTITUENT (INCI Name) | Other Chemical Name |
|---|---|
| SODIUM HYDROXY-METHYLGLYCINATE | Sodium N-(hydroxymethyl)glycinate |
| SODIUM LAURYL SULFATE | Sodium dodecyl sulphate |
| SODIUM METABISULFITE | Disodium disulphite |
| SODIUM METHYLPARABEN | Sodium 4-(methoxycarbonyl)phenolate |
| SODIUM PALMITATE | Sodium palmitate |
| SODIUM PCA | Sodium 5-oxo-L-prolinate |
| SODIUM POLYSTYRENE SULFONATE | Benzenesulfonic acid, ethenyl-, homopolymer, sodium salt |
| SODIUM STYRENE/ACRYLATES COPOLYMER | |
| SODIUM STYRENE/PEG-10 MALEATE/NONOXYNOL-10 MALEATE/ACRYLATES COPOLYMER | |
| SOLUBLE COLLAGEN | |
| SORBIC ACID | Hexa-2,4-dienoic acid |
| SORBITAN OLEATE | Sorbitan oleate |
| SORBITAN STEARATE | Sorbitan stearate |
| SORBITOL | D-glucitol |
| SOYALECITHIN | |
| SQUALENE | 2,6,10,15,19,23-hexamethyltetracosa-2,6,10,14,18,22-hexaene |
| STEARALKONIUM CHLORIDE | Benzyldimethyl(octadecyl)ammonium chloride |
| STEARDIMONIUM HYDROXYPROPYL HYDROLYZED WHEAT PROTEIN | |
| STEARETH-10 ALLYL ETHER/ ACRYLATES COPOLYMER | |
| STEARETH-20 | Poly(oxy-1,2-ethanediyl), a-octadecyl-?-hydroxy |
| STEARETH-21 | Poly(oxy-1,2-ethanediyl), a-octadecyl-?-hydroxy |
| STEARIC ACID | Stearic acid |
| STEARYL ALCOHOL | Octadecan-1-ol |
| STEARYL CAPRYLATE | Octadecyl octanoate |
| STEARYL HEPTANOATE | Octadecyl heptanoate |
| STYRENE/ACRYLATES COPOLYMER | |
| STYRENE/PVP COPOLYMER | 2-pyrrolidinone, 1-ethenyl-, polymer with ethenylbenzene |
| SUCROSE | Sucrose |
| SULFUR | Sulphur |
| TALLOWTRIMONIUM CHLORIDE | Quaternary ammonium compounds, trimethyltallow alkyl, chlorides |
| t-BUTYL ALCOHOL | 2-methylpropan-2-ol |
| TEA-CARBOMER | |
| TETRAHYDROXYPROPYL ETHYLENEDIAMINE | 1,1',1'',1'''-ethylenedinitrilotetrapropan-2-ol |
| TETRASODIUM EDTA | Tetrasodium ethylenediaminetetraacetate |
| THIAMINE HCl | Thiamine hydrochloride |
| THREONINE | L-threonine |
| THYMUS HYDROLYSATE | Protein hydrolyzates, thymus gland. Substance obtained by acidic, alkaline, or enzymatic hydrolysis of thymus gland composed primarily of amino acids, peptides, and proteins. It may contain impurities consisting chiefly of carbohydrates and lipids along w |
| *THYMUS VULGARIS* | Thyme, *Thymus vulgaris*, ext. Extractives and their physically modified derivatives such as tinctures, concretes, absolutes, essential oils, oleoresins, terpenes, terpene-free fractions, distillates, residues, etc., obtained from *Thymus vulgaris*, Labiatae |
| TITANIUM DIOXIDE | Titanium dioxide (CI 77891) |
| TOCOPHEROL | a-tocopherol; 3,4-dihydro-2,5,7,8-tetra-methyl-2-(4,8,12-trimethyltridecyl)-2Hbenzopyran-6-ol |
| TOCOPHERYL ACETATE | a-tocopheryl acetate, 3,4-dihydro-2,5,7,8-tetramethyl-2-(4,8,12-trimethyltridecyl)-2H-benzopyran-6-yl acetate |
| TRIACETIN | Triacetin |
| TRIBEHENIN | Propane-1,2,3-triyl tridocosanoate |
| TRIDECETH-10 | Poly(oxy-1,2-ethanediyl), a-tridecyl-?-hydroxy |
| TRIDECETH-12 | Poly(oxy-1,2-ethanediyl), a-tridecyl-?-hydroxy |
| TRIDECETH-3 CARBOXYLIC ACID | |
| TRIDECETH-7 | |
| TRIDECETH-9 | Poly(oxy-1,2-ethanediyl), a-tridecyl-?-hydroxy |
| TRIDECYL STEARATE | Tridecyl stearate |
| TRIETHANOLAMINE | 2,2',2''-nitrilotriethanol |
| TRIETHYL CITRATE | Triethyl citrate |
| TRIETHYLENE GLYCOL | 2,2'-(ethylenedioxy)diethanol |
| TRILAURETH-4 PHOSPHATE | Poly(oxy-1,2-ethanediyl), a,a',a''-phosphinylidynetris-?-(dodecyloxy)- |

TABLE 1-continued

| CONSTITUENT (INCI Name) | Other Chemical Name |
|---|---|
| TRIMETHYLOLPROPANE | |
| TRIMETHYLSILYLAMODI METHICONE | |
| TRITICUM SATIVUM VULGARE | |
| TRITICUM VULGARE | Starch. High-polymeric carbohydrate material usually derived from cereal grains such as corn, wheat and *sorghum*, and from roots and tubers such as potatoes and tapioca. Includes starch which has been pregelatinized by heating in the presence of water; Oi |
| TUMERIC ROOT | |
| *TUSSILAGO FARFARA* | *Tussilago farfara*, ext. Extractives and their physically modified derivatives such as tinctures, concretes, absolutes, essential oils, oleoresins, terpenes, terpene-free fractions, distillates, residues, etc., obtained from *Tussilago farfara*, Compositae |
| *URTICA DIOICA* | *Urtica dioica*, ext. Extractives and their physically modified derivatives such as tinctures, concretes, absolutes, essential oils, oleoresins, terpenes, terpene-free fractions, distillates, residues, etc., obtained from *Urtica dioica*, Urticaceae |
| VA/CROTONATES/ NEODECANOATE COPOLYMER | |
| VA/CROTONATES/VINYL NEODECANOATE COPOLYMER | Neodecanoic acid, ethenyl ester, polymer with 2-butenoic acid and ethenyl acetate |
| VA/CROTONATES COPOLYMER | 2-butenoic acid, polymer with ethenyl acetate |
| VA/CROTONIC ACID COPOLYMER | |
| VA/VINYL BUTYL BENZOATE/ CROTONATES COPOLYMER | |
| *VACCINIUM MYRTILLUS* | *Vaccinium myrtillus*, ext. Extractives and their physically modified derivatives such as tinctures, concretes, absolutes, essential oils, oleoresins, terpenes, terpene-free fractions, distillates, residues, etc., obtained from *Vaccinium myrtillus*, Ericace |
| VINYL CAPROLACTAM/PVP/ DIMETHYLAMINO-5 ETHYL METHACRYLATE COPOLYMER | |
| VINYLPYRROLIDONE | |
| VISCOCITY CONTROLLING AGENT | |
| *VISCUM ALBUM* | *Viscum album*, ext. Extractives and their physically modified derivatives such as tinctures, concretes, absolutes, essential oils, oleoresins, terpenes, terpene-free fractions, distillates, residues, etc., obtained from *Viscum album*, Loranthaceae |
| *VITIS VINIFERA* | Grape, red, ext. Extractives and their physically modified derivatives such as tinctures, concretes, absolutes, essential oils, oleoresins, terpenes, terpene-free fractions, distillates, residues, etc., obtained from *Vitis vinifera*, Vitaceae; Extractives |
| WATERCRESS EXTRACT | |
| WHEAT AMINO ACIDS | Amino acids, wheat |
| WHEAT GERM EXTRACT | |
| WHEAT GERM GLYCERIDES | Glycerides, wheat germ-oil mono-, di-and tri- |
| HEAT GERMAMIDOPROPYLAMINE OXIDE | Amides, wheat germ, N-(3-dimethylamino-propyl)-N-oxides |
| WHEAT GERMAMIDOPROPYLDIMONIUM HYDROXYPROPYL | |
| HYDROLYZED WHEAT PROTEIN | |
| WHEATGERMAMIDOPROPYL ETHYLDIMONIUM ETHOSULFATE | 1-propanaminium, N-ethyl-N,N-dimethyl-3-antistatic amino-, N-wheat germ acyl derivs., ethyl sulfates |
| XANTHAN GUM | Xanthan gum |
| YOGURT | Naturally occurring substances, milk prepa-biological rations, yogurt |
| *ZINGIBER OFFICINALIS* | Ginger, ext. Extractives and their physically modified derivatives such as tinctures, concretes, absolutes, essential oils, oleoresins, terpenes, terpene-free fractions, distillates, residues, etc., obtained from *Zingiber officinalis*, Zingiberaceae |

In certain embodiments, the hair styling compositions are formulated as a spray. The spray typically includes the active hair care ingredient (fixing agent) and a carrier or propellant. In certain embodiments, the carrier is a water and alcohol mixture. In other embodiments, the spray composition also optionally includes a preservative, antioxidant, sunscreen agent, vitamin, protein, peptide, plant extract, humectant, oil, emollient, lubricant, thickener, hair conditioning agent, polymer, or surfactant. In certain other embodiments, the composition includes an oil, a polymer, a humectant, or a fragrance. In certain particular embodiments, the composition comprises water, an alcohol, an oil, fragrance, and an active hair care ingredient. In certain particular embodiments, the composition comprises water, an alcohol, an oil, a polymer, fragrance, and an active hair care ingredient. In certain particular embodiments, the composition comprises water, an alcohol, an anti-static agent, fragrance, and an active hair care ingredient. In certain particular embodiments, the composition comprises water, an alcohol, a hair-conditioning agent, fragrance, and an active hair care ingredient. In certain particular embodiments, the composition comprises water, an alcohol, a surfactant, fragrance, and an active hair care ingredient. In certain particular embodiments, the composition comprises water, an alcohol, an emollient, fragrance, and an active hair care ingredient. Hair spray compositions are dispensed from containers that are aerosol dispensers or pump spray dispensers. Such dispensers are known in the art and are commercially available from a variety of manufacturers.

In certain embodiments, when the hair spray composition is dispensed from a pressurized aerosol container, a propellant is used to force the composition out of the container. Suitable propellants are described herein. In certain embodiments, the propellant is a liquefiable gas. In certain embodiments, the propellant is a halogenated propellant. In other embodiments, the composition does not contain any fluorinated or chlorinated propellants. Generally, the amount of propellant in the composition is from about 10% to about 60% by weight. In certain embodiments, the amount of propellant in the composition ranges from about 15% to about 50% by weight. In certain embodiments, the propellant is separated from the hair spray composition as in a two compartment container. Other suitable aerosol dispensers are those characterized by the propellant being compressed air which can be filled into the dispenser using a pump or equivalent device prior to use. Such dispensers are described in U.S. Pat. Nos. 4,077,441 and 4,850,577, both of which are entirely incorporated by reference herein, and in U.S. patent application Ser. No. 07/839,648, filed Feb. 21, 1992, also entirely incorporated by reference herein.

Conventional non-aerosol pump spray dispensers, i.e., atomizers, may also be used to apply hair spray compositions.

In certain embodiments, the cosmetic hair care composition is a cream. The inventive cream typically includes the active hair care ingredient, a carrier, an oil, a hair conditioning agent, and a thickening agent. In certain embodiments, the cream also includes a fragrance. In certain embodiments, the cream also includes a plant extract. In certain embodiments, the cream also includes a surfactant. In certain embodiments, the cream also includes a polymer. The example cream may be packaged in a tube, tub, bottle, or other suitable container.

By way of example, a suitable exemplary styling composition comprises the following formulation:

| Ingredients/INCI Name | Approx. w % |
| --- | --- |
| Water | 30-100% |
| 2-Propanone | 1-45% |
| Phenyl Trimethicone | 0-10% |
| Capric/Capryllic Triglyceride | 0-10% |
| Silk Protein Powder | 0-10% |
| Cetyl Alcohol | 0-10% |
| Stearyl Alcohol | 0-10% |
| Cetrimonium Chloride | 0-10% |
| Glyceryl Stearate | 0-10% |
| PEG-150 Distearate | 0-10% |
| Polysorbate-80 | 0-10% |
| DL-Panthenol | 0-10% |
| Cyclopentasiloxane and Dimethicone | 0-10% |
| Quaternium-80 | 1-10% |
| Glycerine | 0-10% |
| *Ricinus Communis* (Castor) Seed Oil | 0-10% |
| *Cannibis Sativa* (Hemp) Seed Oil | 0-10% |
| Silk Protein | 0-10% |
| *Urtica Dioica* (Nettle) Extract | 0-10% |
| *Matricaria Recutita* (Chamomile) Flower Extract | 0-10% |
| *Simmondsia Chinensis* (Jojoba) Seed Oil | 0-10% |
| PropyleneGlycol | 0-10% |
| Iodopropynyl Butylcarbamate, Diazolidinyl Urea | |
| Fragrance | 0-10% |
| Triethanolamine | 0-10% |

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. Such equivalents are intended to be encompassed in the scope of the claims, if appended hereto or subsequently filed.

What is claimed is:

1. A method for treating a keratinous fiber of a mammal, the method comprising:
applying a keratinous fiber styling composition to the keratinous fiber; wherein the styling composition comprises:

a cosmetically suitable carrier;

a polymerizable monomer selected from a member of the group consisting of soy protein and hydrolyzed silk (silk peptide); and at least one protein fixing agent selected from a member of the group consisting of 2-propanone, ethyl lactate, butyl lactate, butanone, t-butanol and n-butanol; and activating the protein fixing agent to initiate an in-situ polymerization reaction on the keratinous fiber by applying heat to the keratinous fiber at a temperature below 300° F.

2. The method of claim 1, wherein the protein fixing agent is activated by a member selected from the group consisting of: warm water, flat iron, blow dryer, heated brush, heated brush with a rotating drum and curling iron.

3. The method of claim 1, wherein the heat is applied to the keratinous fiber for about 1 to 10 seconds.

4. The method of claim 1 wherein the heat is applied to the keratinous fiber at a temperature between 212° F. to below 300° F.

5. The method of claim 1, further comprising a step of washing and rinsing the keratinous fiber prior to applying the styling composition.

6. The method of claim 1, further comprising a step of rinsing the keratinous fiber after about 2-5 minutes.

7. The method claim 1, further comprising a step of blow drying the keratinous fiber prior to applying heat.

8. The method of claim 1, wherein the styling composition further comprises a quaternary ammonium salt.

9. The method of claim 8, wherein the quaternary ammonium salt is quaternium-80.

10. The method of claim 1, wherein the level of protein fixing agent in the styling composition is from about 1 wt % to about 25 wt % of the total composition.

11. The method of claim 1, wherein the level of protein fixing agent in the styling composition is from about 1 wt % to about 10 wt % of the total composition.

12. The method of claim 1, wherein the level of protein fixing agent in the styling composition is from about 1 wt % to about 5 wt % of the total composition.

\* \* \* \* \*